United States Patent [19]

Calfee et al.

[11] Patent Number: 4,803,987

[45] Date of Patent: Feb. 14, 1989

[54] TEMPERATURE RESPONSIVE CONTROLLER FOR CARDIAC PACER

[75] Inventors: Richard V. Calfee, Houston; Robert A. Adkins, Angleton, both of Tex.; Eckhard U. Alt, Munich, Fed. Rep. of Germany; Ross G. Baker, Jr., Houston, Tex.

[73] Assignee: Intermedics, Inc., Angleton, Tex.

[21] Appl. No.: 872,824

[22] Filed: Jun. 11, 1986

[51] Int. Cl.⁴ .................... A61N 1/00; H05G 00/00
[52] U.S. Cl. ........................ 128/419 PG; 128/419 P
[58] Field of Search ................ 128/419 PG, 419 P

[56] References Cited

U.S. PATENT DOCUMENTS

| | | | |
|---|---|---|---|
| 4,344,437 | 8/1982 | Markowitz | 128/419 PG |
| 4,393,877 | 7/1983 | Imran et al. | 128/419 PG |
| 4,436,092 | 3/1984 | Cook et al. | 128/419 PG |
| 4,543,954 | 10/1985 | Cook et al. | 128/419 PG |
| 4,688,573 | 8/1987 | Alt | 128/419 PG |

*Primary Examiner*—Francis Jaworski
*Assistant Examiner*—George Manuel
*Attorney, Agent, or Firm*—Russell J. Egan

[57] ABSTRACT

A controller for variably controlling the pacing rate of a cardiac pacer responsive to temperature which includes a logic and control unit, a parameter communication unit, an analog to digital converter and a temperature sensor. The temperature sensor in the right ventricle or atrium communicates a value related to blood temperature through the analog to digital converter to the logic and control unit. The logic and control unit operates under control of the rate algorithm to calculate a pacing rate value related to variations in the blood temperature. The pacing rate value is calculated as the sum of a reference rate, a natural rate response term, and a dynamic rate response term which contributes rate only in response to physical activity. A step rate response is also added to the calculated pacing rate when predetermined criteria related to the blood temperature and calculated pacing rate indicate the onset of physical activity. Under the control of the rate algorithm, the controller also maintains the level and rate of change of the calculated pacing rate within predetermined limits, and prevents the pacing rate from remaining at the maximum rate limit after physical activity has ceased.

45 Claims, 11 Drawing Sheets

TEMPERATURE RESPONSIVE CONTROLLER FOR CARDIAC PACER

BACKGROUND OF THE INVENTION

1. Field of the Invention

This invention relates generally to the control of cardiac pacemakers, and more particularly to a rate responsive controller adapted to automatically adjust the pacing rate of a cardiac pacemaker responsive to variations in a patient's intracardiac blood temperature.

2. Description of Related Art

Fixed rate, synchronous and demand pacers designed to pace the heart at a predetermined rate associated with a low or moderate level of physical activity are well known. Such pacers are not designed to adjust the pacing rate to provide the increased level of cardiac response needed to support increased physical activity such as work or exercise. As a result, patients using such pacemakers are constrained in the amount of physical activity they may undertake.

A number of pacemaker and pacer control systems have been proposed in the past to address this shortcoming. One group of such systems of particular interest have proposed using various physiological parameters known to vary with physical activity to provide exercise-responsive adjustments to the pacing rate. For example, systems responsive to the oxygen content of the blood (U.S. Pat. Nos. 4,399,820 and 4,202,339 to Wirtzfield), to blood pressure (U.S. Pat. No. 3,828,371 to Purdy; U.S. Pat. No. 3,638,656 to Grandjean), to respiratory volume (U.S. Pat. No. 3,593,718 to Krasner), and to blood pH (U.S. Pat. No. 4,009,721 to Alcidi) have all been proposed to provide exercise-responsive control of pacing rate.

The proposed systems have a number of problems and drawbacks that have limited their acceptance and use. For instance, it has been found that some of the proposed physiological parameters can vary in response to stimuli such as certain medications in addition to increased physical activity, thus occasionally leading to unintended rate response variations. Another problem has been the difficulty in designing a sensor to accurately measure the proposed parameters. Still another problem has been that sensors designed to measure the parameters of interest have been found unsuitable for long term implantation.

Intracardiac blood temperature has also been proposed as a parameter indicative of physical activity to control pacing rate. It has been found that blood temperature provides a more accurate and reliable indication of physical activity than other proposed parameters and that it may be sensed accurately and easily with readily available temperature sensors.

U.S. Pat. Nos. 4,436,092 and 4,543,954 to Cook for example disclose rate responsive pacers in which intracardiac blood temperature is detected by a thermistor inserted intravenously in the right ventricle. The Cook patents relate the detected temperature to a pacing rate by a mathematical formula derived from the experimentally observed relation between heart rate and intracardiac blood temperature in test dogs. The mathematical formula includes a resting rate term, a term related to the difference between current temperature and a fixed reference temperature, and a term related to the rate of change of temperature with respect to time. The Cook '954 patent constrains the calculated pacing rate to one of three discrete values, a high exercise value, a low at-rest value, and an intermediate value.

German Patent No. GM 7606824 to Csapo discloses another temperature responsive pacemaker which utilizes a thermistor located in the heart to control the oscillation rate of a blocking oscillator. The blocking oscillator accordingly generates pacing pulses at a rate related to the intracardiac blood temperature. In another embodiment, the thermistor controls the state of a multivibrator to provide discrete pacing rate levels similar to the Cook '954 patent.

The known temperature responsive pacers, although comprising an improvement over other proposed rate responsive systems, are also subject to a number of drawbacks and deficiencies. For example, studies of the relationship between intracardiac blood temperature and heart rate response in patients with normally functioning hearts indicate (1) that the intracardiac blood temperature and the heart rate vary naturally in a small range over a circadian cycle as well as with fever and the like, and (2) that the beat rate of a normally functioning heart is gradually adaptive to varying levels of physical activity. The rate response of the Cook pacers, however, is based on a single temperature versus time slope term. If the magnitude of the slope term is set to provide adequate exercise response, then natural temperature variations due to fever, the circadian cycle, and the like produce inappropriately large pacing rate adjustments. Therefore, the magnitude of the slope term is designed to be relatively small to provide appropriate rate response for non-activity related temperature variations. Exercise response is provided in the form of a large abrupt addition to the pacing rate.

Also, the Cook algorithm is a function of a single, fixed reference temperature. As a result, the algorithm can produce inappropriate pacing rate calculations if the reference temperature input to the system and used by the algorithm is itself inaccurate and also as the patient's resting blood temperature changes significantly throughout the day.

The prior art rate responsive systems have also lacked various features that provide improved accuracy and safety. For example, one desirable feature not found in the prior art systems is means to control the slew rate or rate of change of the pacing rate. Such control means eliminate abrupt rate variations, which can be harmful to the patient in certain situations, and ensure smooth rate response.

Another desirable feature not found in the prior art systems is means to prevent the rate saturation effect that can occur when the rate response algorithm is capable of providing greater rate response than the desired maximum pacing rate. This can result in the undesirable condition of the pacemaker continuing to pace the heart at the maximum rate even for a period of time after the patient has ceased the physical activity that gave rise to the increased rate response in the first place.

Yet another desirable feature not found in the prior art systems, particularly those such as the Cook '092 system that calculate the rate response as a function of a fixed reference temperature, is means to automatically adjust the reference temperature internally to compensate for any error in the initially supplied value and for naturally occurring changes in the resting temperature. Such adjustment means improves the accuracy of the rate response algorithm without requiring additional intervention by a physician and/or programmer.

In view of the foregoing, it is an object of the invention to provide a rate responsive pacemaker controller that utilizes intracardiac blood temperature as a physiological parameter that provides an accurate indication of physical activity for adjusting pacing rate.

It is another object of the invention to provide such a controller that adjusts the pacing rate in a manner that more accurately approximates the rate response of a normally functioning heart in all metabolic situations by responding to both dynamic temperature increases due to physical exertion and to natural temperature variations related to circadian rhythm, fever, and the like.

It is another object of the invention to provide such a controller that more accurately approximates the rate response of a normally functioning heart by providing gradually adaptive response to varying levels of physical activity.

It is another object of the invention to provide such a controller having an improved rate response algorithm that more accurately approximates the rate response of a normally functioning heart to physical exertion by providing a temporary step-up in pacing rate with the onset of exercise It is still another object of the invention to provide such a controller providing improved detection of the onset of physical activity in conjunction with the provision of a step rate response.

It is yet another object of the invention to provide such a controller that includes the following additional features: (1) controlling the slew rate of the calculated pacing rate to prevent abrupt rate variations and to provide smoother rate response than prior art systems, (2) monitoring and preventing the occurrence of rate saturation to provide improved accuracy in the rate response, particularly to the cessation of strenuous physical activity, and (3) automatically adjusting the reference temperature utilized by the rate response algorithm to compensate for any error in the initially supplied value of the reference temperature.

SUMMARY OF THE INVENTION

The foregoing objects and attendant advantages are achieved by providing a temperature responsive pacer controller having an element that determines the blood temperature and a control unit that calculates a pacing rate related to the sensed blood temperature. The control unit utilizes an improved rate response algorithm to periodically calculate a natural heart rate response, a dynamic heart rate response, and a step rate response related to the sensed temperature. The control unit may combine various response terms to obtain a desired pacing rate. The calculated pacing rate is then communicated to a pacing pulse output unit. In addition, the control unit monitors the rate of change and the level of the calculated pacing rate and maintains them within predetermined limits.

BRIEF DESCRIPTION OF THE DRAWING

The novel features that are believed to be characteristic of the invention are set forth in the appended claims. The presently preferred embodiments of the invention, together with further objects and attendant advantages, will be best understood by reference to the detailed description that follows, together with the appended drawing, in which:

DETAILED DESCRIPTION OF THE PRESENTLY PREFERRED EMBODIMENTS

Figure 1:
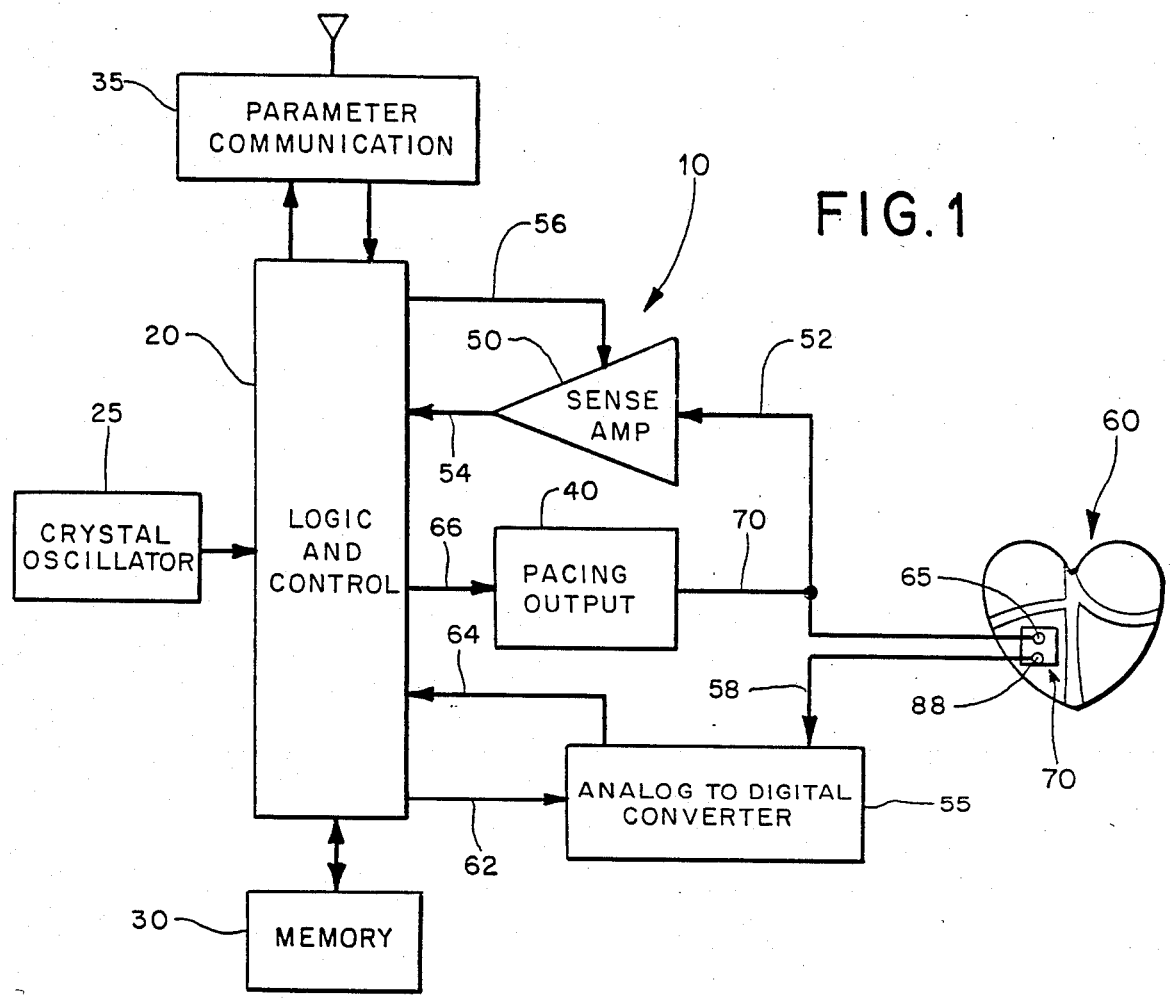
FIG. 1 is a block diagram generally illustrating the components of the preferred temperature responsive controller.

With reference to the drawing, FIG. 1 illustrates a block diagram of a presently preferred embodiment of the temperature responsive controller. As shown, the temperature responsive controller 10 includes a logic and control unit 20 which is preferably a digital microprocessor. Although other circuit forms such as analog or discrete digital logic could also be employed, a microprocessor is preferred for its small size and flexibility. A particularly energy efficient microprocessor designed for use as an implanted pacer controller is described in U.S. Pat. No. 4,404,972 which is assigned to the assignee of this application. The microprocessor disclosed in the '972 patent constitutes a particularly preferred embodiment of the logic and control unit 20 and accordingly the disclosure of the '972 patent is hereby incorporated by reference. A conventional crystal oscillator 25 drives the logic and control unit 20 in the preferred digital embodiment.

Memory 30 interfaces with the logic and control unit 20 in a conventional manner. Memory 30 preferably includes ROM for storing operating program instructions and other programs such as a pacer algorithm and the preferred rate algorithm described below. Memory 30 preferably also includes RAM for storing data and various algorithm parameters also described in detail below.

A parameter communication unit 35 provides an interface for transferring parameter data between an external programmer (not shown) and the logic and control unit 20 via telemetry. The construction and use of the external programmer and the communication unit 35 are known to those skilled in the art and further description thereof is not necessary to a complete understanding of the invention. One known programmer and communication unit combination which is suitable for use is described in Calfee et al. U.S. Pat. No. 4,539,992 which is assigned to the assignee of this application.

One end of a pacing/sensing lead 70 contains a pacing/sense electrode 65 and a temperature sensor such as thermistor 88 and is preferably positioned in either the right atrium or ventricle of the heart 00. Satisfactory results are obtained with the lead 70 located in either chamber. The chamber in which the lead 70 is positioned is determined by the patient's physician based on the patient's particular condition. However, it is preferable regardless of which chamber the lead 70 is positioned in that the thermistor 88 be located near the tricuspid valve. The blood near this valve is an optimal mixture of blood from the upper and lower extremities, and the temperature of the blood at this point is an average temperature which provides an accurate indication of the average total work being done by the patient. Thus, the voltage across the thermistor 88 in the preferred location provides an accurate indication of the average blood temperature. This temperature is ultimately used by the rate algorithm to calculate the appropriate pacing rate in a manner described in detail below. The construction of the lead 70 itself is not critical to the invention, various suitable lead arrangements being known to those skilled in the art. See, for example, U.S. Pat. No. 4,543,954 to Cook.

A conventional sense amplifier 50 receives ECG signals on line 52 from the pacing/sense electrode 65. The sense amplifier 50 communicates a signal indicating the detection of a heart beat to the logic and control unit 20 on line 54. The logic and control unit 20 can enable and disable the sense amplifier 50 through signals transmitted to the sense amplifier 50 on line 56.

An analog to digital converter 55 receives the thermistor analog voltage signal on a line 58. The logic and control unit 20 sends digital temperature and calibration data, control codes, and address information to the analog to digital converter 55 on bus 62. The analog to digital converter 55 signals the logic and control unit 20 on line 64 when the digital temperature data on the bus 62 corresponds to the analog voltage signal of the thermistor 88.

The logic and control unit 20 outputs pulse parameters including amplitude, width, and rate as calculated by the rate algorithm, and control signals on line 66. A conventional pacing output unit 40 receives the pulse parameters and control signals and generates pacing pulses according thereto which are conducted through lead 70 to the pacing/sense electrode 65. Many programmable pacing output units suitable for use herein are known to those skilled in the art. Detailed description of such units herein is not deemed necessary to an understanding of the invention.

A general description of the operation of the system thus far described will now be given. A detailed description of a preferred rate calculation algorithm follows below.

Initially, a physician or programmer, for example, uses the external programmer (not shown) to transmit selected pacing pulse and rate algorithm parameters appropriate for the patient to the temperature responsive controller 10. The parameter communication unit 35 receives the parameters and communicates them to the logic and control unit 20 which stores them in memory 30.

In the preferred embodiment, the logic and control unit 20 operates cyclically under the control of an operation program stored in memory 30. In the preferred form described in U.S. Pat. No. 4,404,972, the logic and control unit 20 is active during a portion of the cycle and inactive during the remainder of the cycle. During the active portion, the logic and control unit 20 performs a number of functions under program control. Such functions include, among others, determining pacing rate according to the rate algorithm and controlling the pacing output unit 40 in accordance with a pacing algorithm.

Under control of the pacing algorithm, the logic and control unit 20 may control the pacing output unit 40 to perform fixed rate, synchronous, or demand pacing functions in either a single or dual chamber sensing and pacing arrangement. Although FIG. 1 illustrates a single chamber sensing and pacing arrangement, the illustration is deemed exemplary rather than critical and use in dual chamber sensing and pacing applications is equally contemplated by the invention. Various single and dual chamber pacing and sensing modes are well known to those skilled in the art and do not require description for a full understanding of the invention.

Under the control of the temperature responsive rate algorithm, the logic and control unit 20 determines the corresponding digital value of the current measured intracardiac blood temperature from the analog to digital converter 55, calculates a pacing rate value and a number of associated values related thereto, and stores the calculated pacing rate and associated values in memory 30, all as described in detail blow.

When the logic and control unit 20 has completed the preprogrammed functions in the active portion of the cycle, it enters the inactive portion of the cycle. After the inactive portion of the cycle terminates, it again enters the active portion of the cycle and repeats the functions called for by the pacing and rate algorithms and other programs stored in memory 30.

Figure 2:
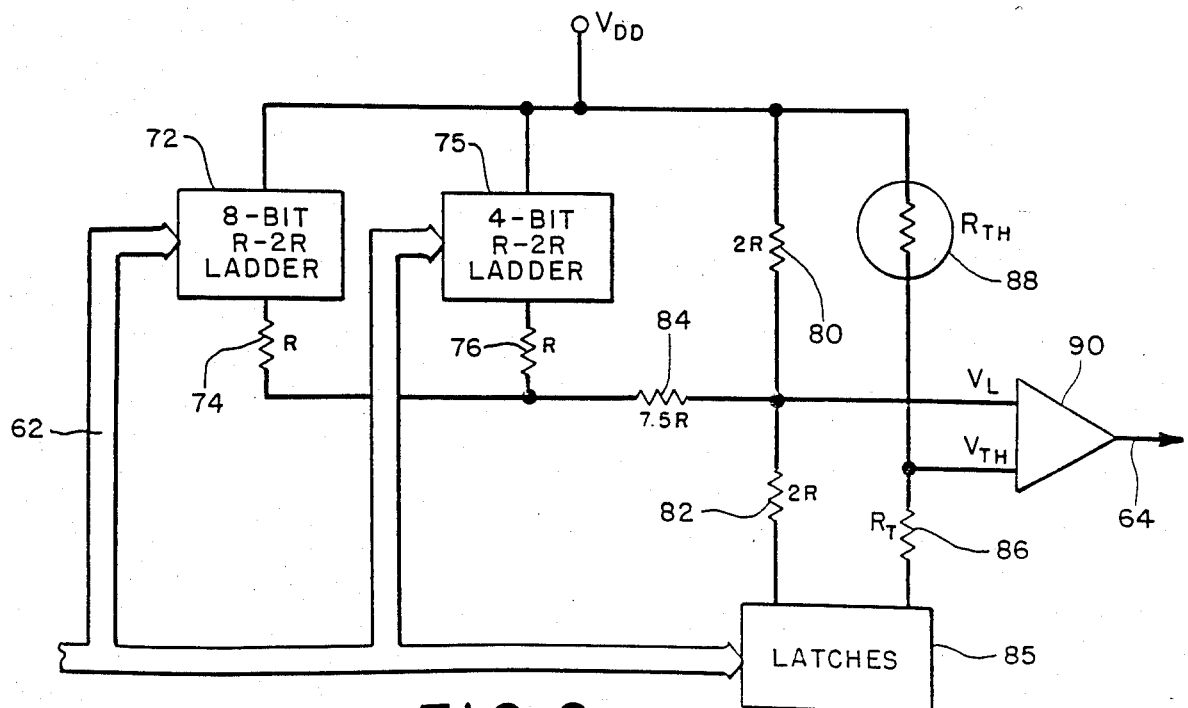
FIG. 2 is a schematic diagram illustrating the details of the analog to digital converter block of FIG. 1.

FIG. 2 is a schematic diagram illustrating the details of a presently preferred embodiment of the analog to digital converter 55. As shown, an 8-bit R-2R ladder 72 and a 4-bit R-2R ladder 75 are connected in parallel at one end to a positive voltage source Vdd and at the other end to the non-inverting terminal of a comparator 90 through respective parallel resistors 74 and 76 each having a relative value of R and a series resistor 84 having a relative value of 7.5R. The 8-bit and 4-bit ladders 72 and 75 receive digital input values DW0–DW7 and DA0–DA3, respectively, from the logic and control unit 20 on the bus 62. The input values are preferably latched to the ladders by conventional latches (not shown) having tri-stated outputs.

A voltage divider comprised of resistors 80 and 82 having respective relative values 2R and 2R is connected between the positive voltage source Vdd and latches 85. Latches 85 preferably have tri-stated outputs which may be controlled by signals from the logic and control unit 20 on bus 62. The junction of the resistors 80 and 82 is connected to the non-inverting terminal of the comparator 90. A second voltage divider comprised of thermistor 88 and resistor 86 is also connected between Vdd and latches 85. Resistor 86 and thermistor 88 have relative values of $R_T$ and $R_{TH}$ respectively. The junction of series thermistor 88 and resistor 86 is connected to the inverting terminal of the comparator 90. The comparator 90 output is connected to the logic and control unit 20 by line 64. The ladders 72 and 75, the latches 85, and the comparator 90 each have a standard low voltage connection Vss (not shown) as well.

With the exception of the thermistor 88 and resistor 86, the analog to digital converter 55 is preferably embodied in an integrated circuit (IC) which is suitably constructed according to conventional methods now known and used by those skilled in the art. Comparator 90 is easily constructed on the IC as a conventional comparator. However, it is difficult to form resistive components having absolute values within acceptable tolerances in an IC. It is easy, however, to form resistive components which have values that are accurately scaled with respect to one another. Accordingly, an IC having resistive components with the relative values illustrated in FIGS. 2 and 3 and a nominal value for R of 500K ohms comprises a presently preferred embodiment of the analog to digital converter 55.

The thermistor 88 selected for use preferably has a temperature coefficient sufficient to provide response over the temperature range of interest. In the presently preferred embodiment a nominal temperature range of 36-40 degrees C. has been selected. In addition, the thermistor 88 is selected to have a nominal resistance value that minimizes the current drawn by the analog to digital converter 55 while also holding down the RC time constant created by the thermistor 88 and the capacitance of the pacing/sensing lead. An example of a thermistor having the desired characteristics is the Thermometrics Model BR16 thermistor which has a nominal resistance of 75K ohms at 37.00 degrees C. and which has been found suitable.

Resistor 86 is selected both to provide linearization of the thermistor 88 response and to match the thermistor response to the range of the 8-bit ladder 72. The value $R_T$ selected for resistor 86 determines where in the range of the 8-bit ladder 72 the nominal value of the thermistor 88 will fall. Given the nominal value of the BR16 thermistor, an $R_T$ of 71.5K ohms has been selected for use in the presently preferred embodiment.

The thermal coefficient of the thermistor 88 and the value of resistor 84 determine the sensitivity and resolution of the converter over the selected temperature range. Given the nominal specification values of the BR16 thermistor and the 7.5R value of resistor 84, it has been calculated that the 8-bit ladder 72 provides a resolution of 0.021 degrees C. per bit and that 190 increments of the 8-bit ladder are needed to cover the nominal temperature range of 36-40 degrees C.

Different values for resistor 86, and for thermistor 88, as well as different nominal temperature ranges may of course be substituted. Such modifications may however change the sensitivity and resolution of the converter. The resolution of the converter can be determined by first determining the voltage $V_{TH}$ at the inverting terminal of the comparator 90 at the upper and lower limits of the nominal temperature range with respect to Vss. The voltage $V_{TH}$ with respect to Vss is determined by the voltage divider comprised of the thermistor 88 and the resistor 86. Therefore, $V_{TH}$ will depend on the resistance of the thermistor 88 at the upper and lower temperature limits and the value $R_T$ chosen for resistor 86. Next, the number of increments on the 8-bit ladder 72 needed to produce an equivalent voltage $V_L$ with respect to Vss at the non-inverting terminal of the comparator 90 at the upper and lower temperature limits is calculated according to the formula:

$$V_L = Vss \frac{8 + \frac{1}{256} \sum_{n=0}^{7} a_n 2^n + \frac{1}{16} \sum_{n=0}^{3} b_n 2^n}{18}$$

Where
  $V_L$=The desired ladder voltage at the non-inverting terminal of the comparator 90;
  Vss=The value of the positive supply voltage;
  $a_n$=The values (0 or 1) of the individual bits 0-7 on the 8-bit ladder; and
  $b_n$=The values (0 or 1) of the individual bits 0-3 on the 4-bit ladder.

It is understood that the term $$\frac{1}{16} \sum_{n=0}^{3} b_n 2^n$$

is a constant value for purposes of this calculation and that the term $$\sum_{n=0}^{7} a_n 2^n$$

provides the number of bit increments necessary to generate a particular desired ladder voltage $V_L$. The difference in the number of increments needed at the upper and lower limits corresponds to the number of bits required to cover the nominal range. Dividing the nominal temperature range by the calculated number of bits gives the resolution of the 8-bit ladder 72 in degrees C. per bit.

After the nominal temperature range is selected and the resolution of the 8-bit ladder 72 calculated, each unique 8-bit value DW0-DW7 on the ladder corresponds to a temperature increment between the upper and lower limits if the values of the various components of the converter exactly equal their specified values and no drift is present in the comparator 90. Since this is unlikely, the 4-bit ladder 75 is used to calibrate the response of the 8-bit ladder 72 to compensate for component tolerances and offset. Initially, a value DW0-DW7 on the 8-bit ladder 72 is selected to correspond to a known temperature within the nominal range. In the presently preferred embodiment, an 8-bit input value DW0-DW7 between 40-50H (hexadecimal) is chosen to correspond to the temperature 37.00 degrees C. Although many other corresponding input and temperature pairs could also be selected, 37.00 degrees C. was selected for the preferred embodiment because it is the nominal blood temperature of a person at rest. The value of 40-50H was chosen because it is approximately one fourth of the way through the range of the 8-bit ladder 72 and correlates to 37.00 degrees C. which is one fourth of the way through the nominal temperature range of 36–40 degrees C.

Once the input value and temperature pair is selected, the response of the 8-bit ladder 72 is calibrated by first determining the patient's temperature, and then inputting the corresponding input value DW0–DW7 to the 8-bit ladder 72. If all component values are as specified, alternately incrementing and decrementing the input value should cause the output of the comparator 90 on line 64 to toggle on and off. If the logic and control unit 20 does not detect the comparator output on line 64 toggling on and off, then it increments the 4-bit input value DA0–DA3 on the 4-bit ladder via bus 62 until alternately incrementing and decrementing the selected 8-bit input value DW0–DW7 causes the comparator output to toggle on and off.

Operation of the preferred analog to digital converter 55 will now be described briefly in view of the foregoing detailed description. Initially, the logic and control unit 20 calibrates the analog to digital converter 55 in the manner described above and latches the 4-bit calibration value DA0–DA3 into the 4-bit ladder 75. This can be done for example as part of a start up routine after power is first applied or in response to a command transmitted from the external programmer. When it is desired to take a temperature reading, the logic and control unit 20 addresses the converter 55 and latches an 8-bit temperature value DW0–DW7 into the 8-bit ladder 72. This turns on the output of the latches 85 and allows current to flow through the thermistor 85, the ladders 72 and 75, and the bias resistors 80 and 82. After a short delay to allow the thermistor 88 to stabilize, the logic and control unit 20 tests the output 64 of the comparator 90 and turns off the outputs of the latches to inhibit further current flow. If the comparator output is high, then the current intracardiac blood temperature is greater then the 8-bit input value DW0–DW7. The logic and control unit 20 alternately increments the input value and tests the comparator 90 output 64 until the state of the comparator 90 changes to indicate that the input value is now greater than the current temperature. The logic and control unit 20 takes the previous input value as indicating the current blood temperature.

The digital value of the current temperature is determined in like manner when the output of the comparator is initially low, except that the logic and control unit 20 decrements the input value until it detects a state change in comparator 90. It should be apparent to those skilled in the art that many different methods are available for finding the digital temperature value with a minimum number of comparisons. Successive approximation, for example, is one such method.

Figure 3:
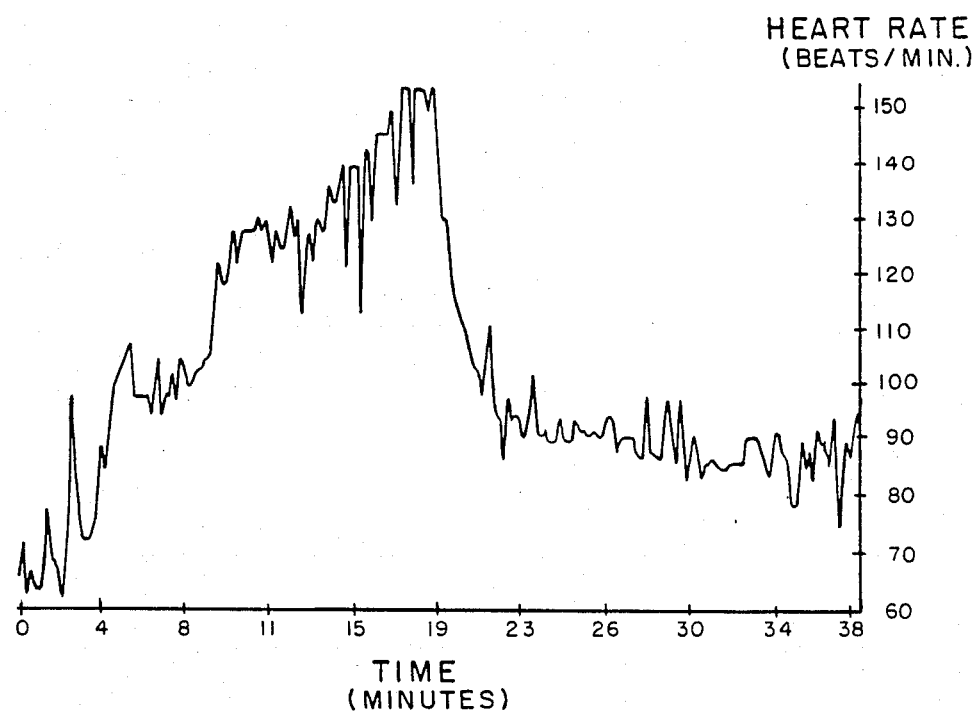
FIG. 3 is a plot based on experimental data illustrating a typical relationship between intracardiac blood temperature and heart rate in a normally functioning heart in response to moderate exercise.
Figure 3:
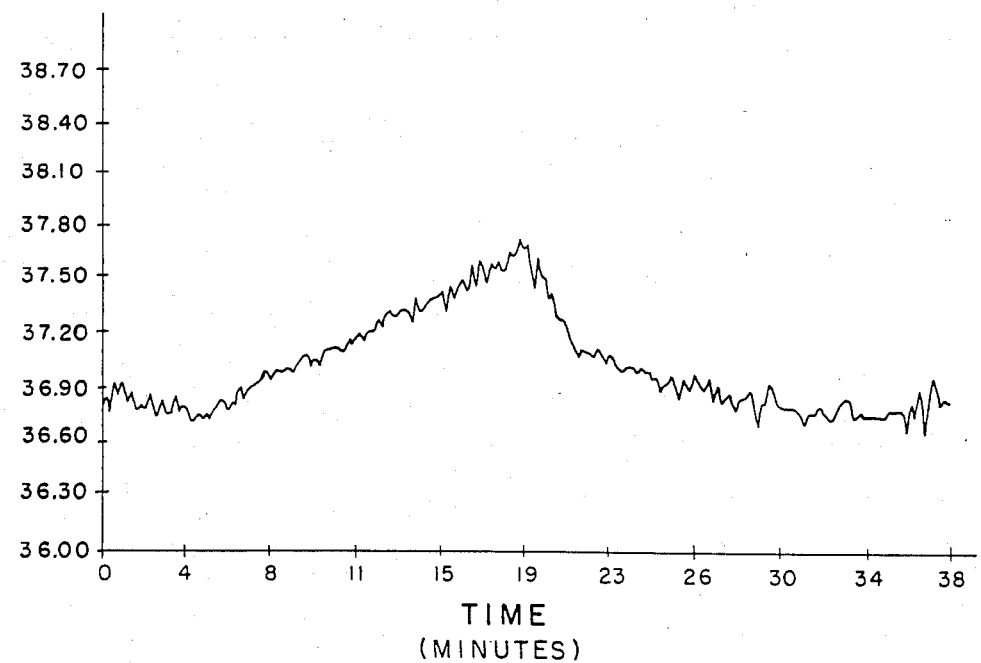

FIG. 3 is a plot based on experimentally obtained data illustrating a typical relationship between heart rate and intracardiac blood temperature in a normally functioning heart in response to moderate exercise. Prior to time zero, the subject has been at rest. The intracardiac blood temperature is typically near 37 degrees C. At zero minutes physical exercise begins. The heart rate immediately begins an upward trend and circulation of relatively cooler blood from other parts of the body through the heart causes an initial drop in the overall intracardiac blood temperature between approximately zero and four minutes in this particular illustration. As the physical exertion continues between approximately four and nineteen minutes, the subject's heart rate continues to rise, at first rapidly and after a time more gradually. The overall intracardiac blood temperature also continues to rise relatively steadily. After approximately nineteen minutes, the physical activity stops. At this point the heart rate and blood temperature stop rising and begin to fall. After approximately thirty eight minutes, blood temperature has nearly returned to its pre-exercise level. Heart rate, however, remains somewhat elevated.

Figure 4:
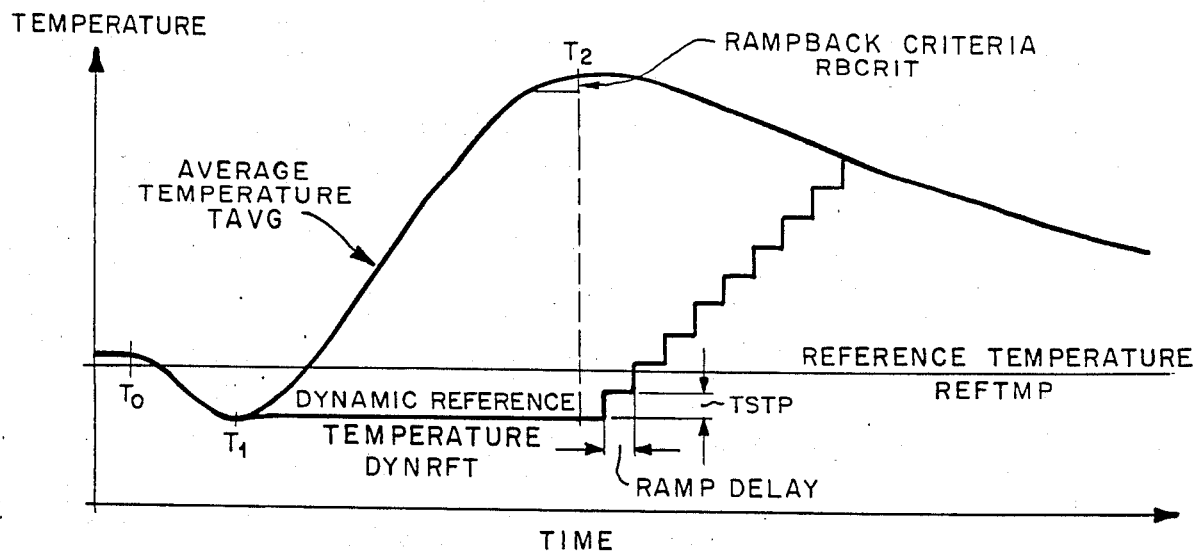
FIG. 4 is a graph of average blood temperature with respect to time in response to physical exertion which has been somewhat smoothed and exaggerated to illustrate the response of various parameters of the preferred rate response algorithm.

The discussion will now turn to a presently preferred algorithm for calculating pacing rate related to the average intracardiac blood temperature. Reference will be had from time to time to FIG. 4, which is a graphical illustration of average blood temperature versus time in response to exercise, and which has been somewhat smoothed and exaggerated both to facilitate discussion and to better illustrate various parameters of the preferred algorithm. The presently preferred rate response algorithm is generally as follows:

Rate=Reference Rate+Natural Rate Response+Dynamic Rate Response+Step Rate Response where:
Reference Rate is a desired base pacing rate;
Natural Rate Response is the desired change in the pacing rate at rest with a change in blood temperature due to natural causes such as the circadian rhythm;
Dynamic Rate Response is the desired change in pacing rate for a change in blood temperature related to physical activity; and
Step Rate Response is the desired immediate step change in pacing rate with the onset of physical activity.

The reference rate term is initially input as a parameter by a physician or programmer in the manner described above and is stored by the logic and control unit 20 in memory 30. The reference rate establishes a baseline pacing rate which typically corresponds to the heart rate of the patient at rest, although in particular cases the physician may wish to set a higher or lower reference rate. A typical value for the reference rate is 70 beats per minute.

The natural rate response term approximates the rate response of a normally functioning heart to gradual variations in blood temperature due to the natural temperature cycle of the body, fever, and the like. The natural rate response term can vary the pacing rate up or down depending on whether the average intracardiac blood temperature (TAVG) is greater than or less than the reference temperature (REFTMP), which is illustrated in FIG. 4. The natural rate response term is calculated as follows:

Natural Rate=KNATP * (TAVG−REFTMP) if TAVG−REFTMP is positive, and

Natural Rate=KNATN * (TAVG−REFTMP) if TAVG−REFTMP is negative, where:
TAVG is the current average temperature of the intracardiac blood calculated from periodic temperature readings;
REFTMP is a reference temperature parameter;
KNATP is a positive natural rate coefficient; and
KNATN is a negative natural rate coefficient.

The reference temperature REFTMP and the coefficients KNATP and KNATN are initially input by a physician or programmer. REFTMP is in units of degrees C. and has a typical value of 37 degrees C. The coefficients KNATN and KNATP are in units of beats per minute per degree C. A typical value for KNATP is 12 beats per minute per degree C. A typical value for KNATN is 6 beats per minute per degree C.

Figure 5:
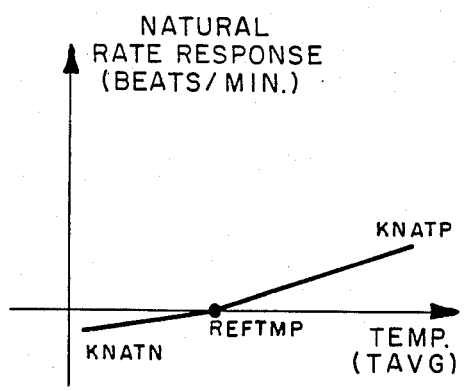
FIG. 5 is a graphical representation of the natural rate response function of the preferred rate algorithm of the temperature responsive controller.

FIG. 5 illustrates the natural rate response function. Given the preferred values of KNATP and KNATN, the natural rate response is linear in the positive and negative directions individually even though the overall function is not linear. It should be apparent from the above and from FIG. 5 that the natural rate response always contributes to the calculated pacing rate value unless the average temperature TAVG is equal to the reference temperature REFTMP.

Although REFTMP is illustrated as a straight line in FIG. 4, it is actually preferred for the controller to periodically recalculate REFTMP internally as a log term weighted average. Periodically recalculating REFTMP internally as a long term weighted average compensates for any miscalculation or other error that may have occurred in initially setting REFTMP. Moreover, recalculating REFTMP compensates for natural daily variations in the resting temperature. As a result, a more accurate REFTMP and more accurate rate calculations are obtained. REFTMP is periodically calculated according to the following formula:

REFTMP=$A_N$ where $A_N = K * S_{N-1}$ $D_N = TAVG - A_N$ $S_N = S_{N-1} + D_N$ and:

$A_N$ is the current weighted average temperature over a predetermined time period;
K is a constant coefficient of $\frac{1}{2}n$ which determines the length of time over which temperature is averaged;
$S_N$ is the current sum of the previous average weighted sum and the deviation between current TAVG and the weighted average temperature over the averaging time;
$D_N$ is the deviation between current TAVG and the weighted average temperature $A_N$;
$S_{N-1}$ is the previous average weighted sum; and
n is an integer value between 8 and 24.

Initially a physician or programmer inputs a value for $S_N$ which corresponds to the REFTMP initially desired and which might correspond to 37 degrees C., for example. $S_N$ is initially set to $A_N/K$ or $2^n A_N$ or $2^n(REFTMP)$ Thereafter, $A_N$ is periodically recalculated by determining the deviation $D_N$ between the current TAVG and the current value of $A_N$, adding the difference $D_N$ to the previous weighted sum $S_{N-1}$ to get a current weighted sum $S_N$, and multiplying the previous sum $S_{N-1}$ by the constant K to obtain a new $A_N$ which becomes the new value of REFTMP. Thus, the new $A_N$ is based on the weighted sum calculated in the previous recalculation cycle.

The value selected for n determines the value of K and the averaging time constant $\tau$. The time constant $\tau$ is related to K by the function $\tau 32\ T/K$, where T is how often a new TAVG is calculated. Thus, for example, assuming a pacing rate of 70 beats per minute and a new, TAVG calculation every four beats, as is preferred, a K value of $\frac{1}{2}^8$ corresponds to an averaging time constant of approximately 14.5 minutes and a K value of $\frac{1}{2}^{24}$ corresponds to a time constant of approximately 94.3 weeks. The weighted average temperature is related to the current measured temperature with respect to time by the following exponential equation:

$A_t = E*(1 - e^{-t/\tau})$ where:

t=a given moment of time;
$A_t$=the average weighted temperature at a given moment of time t;
E=the current measured temperature; and
$\tau$=the averaging time constant.

From the foregoing it will be apparent to those skilled in the art that the weighted average temperature $A_N$ approaches the current measured temperature exponentially and with a time constant $\tau$. The time constant $\tau$ of the exponential function effects a weighted averaging of temperature variations. The greater the value of $\tau$, the less weight assigned to temperature variations of short duration and the longer the time for $A_N$ to approach the measured temperature. Conversely, for smaller values of $\tau$, short term variations have relatively greater weight and $A_N$ approaches the current measured temperature faster.

Whereas the natural rate response term always contributes to the calculated pacing rate value when the average blood temperature TAVG varies from the reference temperature REFTMP, the dynamic rate response term only contributes to the pacing rate value when there is an indication of physical exertion that requires additional rate response. The amount of rate response contributed by the dynamic rate response term is determined in part by a second reference temperature variable DYNRFT. DYNRFT, unlike REFTMP is not initially input as a parameter by a physician or programmer but is always calculated by the preferred rate algorithm internally. Also, unlike REFTMP, DYNRFT varies dynamically to track the average blood temperature TAVG during periods of inactivity and remains constant during periods when the blood temperature is increasing due to physical activity.

As illustrated in FIG. 4, up until time $T_1$ as TAVG remains steady and then drops with the onset of physical activity, DYNRFT tracks TAVG. After time $T_1$ as TAVG rises with continued physical activity, DYNRFT remains constant. DYNRFT remains constant as long as the rate of increase of TAVG exceeds a minimum value established by the rampback criteria parameter RBCRIT. The value of RBCRIT, which might typically be zero, is initially input by a physician or programmer. At time $T_2$, when the patient reduces and stops his physical activities, the rate of increase of TAVG drops below the RBCRIT value. At this point, DYNRFT begins to ramp back toward TAVG. DYNRFT is periodically incremented by an amount TSTP. Each increment TSTP is delayed by an amount established by a RAMP DELAY parameter. The parameters TSTP, which is in units of degrees C., and RAMP DELAY, which is a counter value, are initially input by the physician or programmer. When DYNRFT again equals or exceeds TAVG, it is set equal to TAVG. So long as TAVG rises at a rate below RBCRIT, remains steady, or drops, DYNRFT will continue to track it. If TAVG should again begin to rise at a rate greater than RBCRIT, as may occur during periods of intermittent exercise and rest, DYNRFT remains constant at its current value until the rate of rise of TAVG again falls below RBCRIT.

From the foregoing it should be apparent that the values selected for TSTP and RAMP DELAY determine how rapidly DYNRFT reacts at the end of exercise to resume tracking TAVG. It will become apparent below that this also determines how rapidly the dynamic rate response decays after the end of exercise.

The dynamic rate response term is preferably calculated as follows:

If (TAVG−DYNRFT)<BP1, then Dynamic Rate Response=KP0 *(TAVG−DYNRFT);

If (TAVG−DYNRFT)≧BP1 and <BP2, then Dynamic Rate Response=RADJ1+KP1 * (TAVG−DYNRFT);

If (TAVG−DYNRFT)≧BP2, then Dynamic Rate Response=RADJ2 KP2 * (TAVG−DYNRFT);

where,

TAVG is the average intracardiac blood temperature;

DYNRFT is the dynamic reference temperature described above;

KP0 is a first exercise coefficient associated with a temperature differential less than BP1;

KP1 is a second exercise coefficient associated with a temperature differential equal to or greater than BP1 and less than BP2;

KP2 is a third exercise coefficient associated with a temperature differential equal to or greater than BP2;

RADJ1 is a first constant associated with a temperature differential equal to or greater than BP1 and less than BP2;

RADJ2 is a second constant associated with a temperature differential equal to or greater than BP2;

BP1 is a first temperature differential break point; and

BP2 is a second temperature differential break point.

Figure 6:
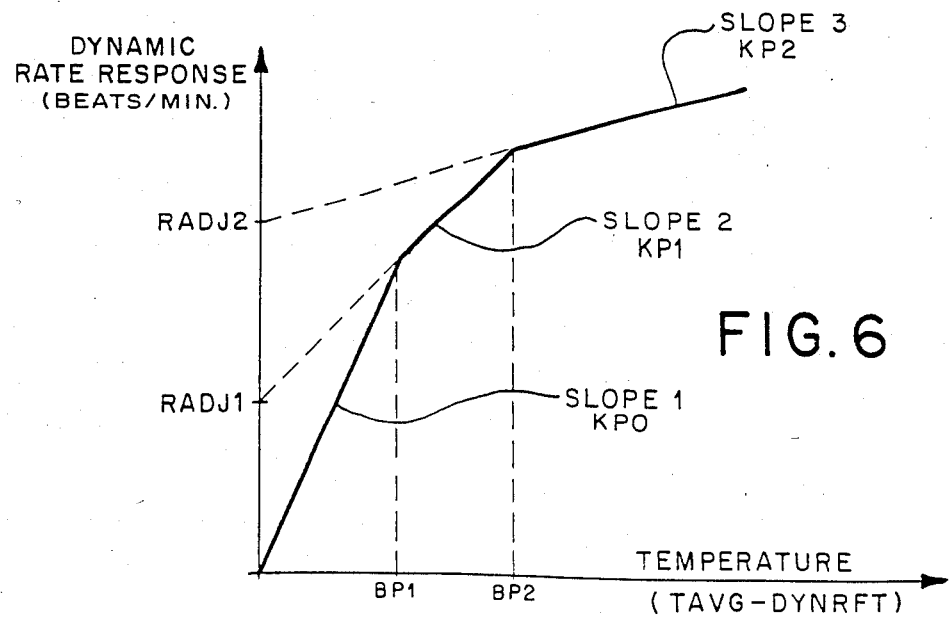
FIG. 6 is a graphical representation of the dynamic rate response function of the preferred rate algorithm of the temperature responsive controller.

FIG. 6 graphically illustrates the dynamic rate response calculated as described above. As shown, the preferred dynamic rate response is a continuous function of the difference between TAVG and DYNRFT. The parameters BP1, BP2, KP0, KP1, KP2, RADJ1, and RADJ2 are initially calculated and input by a physician or programmer. The values of the parameters are selected to provide a continuous function approximating the rate response of a normally functioning heart to exercise as illustrated in FIGS. 3 and 4. Although only three slope segments are illustrated in FIG. 6, it will be apparent to those skilled in the art that a greater or lesser number of slope segments and break points could be used to obtain more or less accurate approximations of the actual heart rate response. Typical values of the parameters are as follows:

KP0=90 beats/minute/degree C.
KP1=66 beats/minute/degree C.
KP2=48 beats/minute/degree C.
BP1=0.3 degree C.
BP2=0.6 degree C.
RADJ1=27 beats/minute
RADJ2=46.8 beats/minute.

It should also be apparent from the foregoing and from FIGS. 4 and 6 that the amount which the dynamic rate response term contributes to the calculated pacing rate value is determined by the correspondence between TAVG and DYNRFT. Thus, when the patient is at rest and DYNRFT is equal to TAVG, the dynamic rate response term does not contribute to the calculated pacing rate value. As the patient begins to exercise and TAVG rises at a rate greater than RBCRIT, the difference between TAVG and DYNRFT increases. While the difference is less than BP1, the dynamic rate response term contributes an amount determined by the first segment of the function illustrated in FIG. 6 and calculated above. When the difference is greater than BP1 and less than BP2, the dynamic rate response term contributes an amount determined by the second segment. When the difference is greater than BP2, the dynamic rate response term contributes an amount determined by the third segment.

When the patient stops exercising and the rate of rise of TAVG falls below RBCRIT, DYNRFT is incremented according to the parameters TSTP and RAMP DELAY as described above and ramps back toward TAVG. As DYNRFT increases and TAVG decreases, the temperature differential decreases and the amount contributed by the dynamic rate response term gradually and continuously decreases according to the function illustrated in FIG. 6. When DYNRFT and TAVG again become equal, no further contribution to the overall rate is made by the dynamic rate response term.

If the patient should again begin exercising, the contribution of the dynamic rate response term would again increase continuously and gradually according to the function of FIG. 6. Regardless of whether the renewed activity begins prior to or after DYNRFT and TAVG becoming equal, the rate of increase is smooth and gradual because the rate response is a continuous function of the difference between TAVG and DYNRFT. Thus, although it is not strictly necessary that the dynamic rate response function be continuous, it should be apparent that a continuous response function provides smoother rate response to varying levels of physical activity, during periods of intermittent exercise and rest, for example, and accordingly is preferred.

In addition to the dynamic rate response term which gradually provides additional rate response with increasing physical activity, it is desirable to provide a significant increase in pacing rate immediately upon detecting the onset of increased activity as in a normally functioning heart as illustrated in FIG. 3. The step rate response term provides an immediate step up in the calculated pacing rate in response to the characteristic dip in blood temperature that is indicative of the onset of increased physical activity. This characteristic dip is illustrated graphically in FIG. 4 and can also be seen between zero and four minutes in the plot of FIG. 3.

To ensure that a sensed drop in blood temperature is the result of the onset of physical activity rather than the result of stopping such activity or some other cause, five predetermined step criteria are tested before the step response is activated. The preferred step criteria and the step response activation algorithm are expressed as follows:

```
If  ((TAVG − DYNRFT) < STPCRIT)
Then
   If  T_CTR ≠ 0
   Then   decrement T_CTR
   Else
        If    ((TL − TAVG) > DIPSLOPE) and
           ((TPEAK − TAVG) > DIPSIZE) and
           (RATE < STPCRTR)
```

```
        Then
            STEP_RESPONSE = STEP SIZE
            STEP_DURATION = STEP DURATION MAX
        Endif
    Endif
Else
    T_CTR = MAX_COUNT
Endif
``` where
  TPEAK K is a peak TAVG value calculated as follows:
  If (TNL<TAVG) then TPEAK=TAVG;
  TNL is the average intracardiac blood temperature from the previous rate calculation cycle;
  TAVG is the current average intracardiac blood temperature;
  DYNRFT is the current value of the dynamic reference temperature;
  STPCRIT is a criteria related to the difference between the average temperature and dynamic reference temperature that ensures that a step response is not provided when the dip is not due to the initial onset of exercise;
  T_CTR is a counter associated with the (TAVG—DYNRFT) criteria that ensures the patient has been at rest for a predetermined period before a step response can be activated;
  TL is the average intracardiac blood temperature from the previous differential cycle;
  DIPSLOPE is the dip criteria related to the slope or rate of change of the dip in average temperature;
  DIPSIZE is the dip criteria related to the magnitude of the dip in average temperature;
  RATE is the present calculated pacing rate;
  STPCRTR is a criteria related to the present calculated pacing rate that ensures a step response is not provided when the pacing rate indicates that the dip is not due to the onset of exercise;
  STEP_RESPONSE is the step rate adjustment to be contributed to the overall rate value;
  STEP_SIZE is the size of the adjustment to be made in beats per minute;
  STEP_DURATION and STEP_DURATION_$MAX$ are counter values that determine how long the step rate response will contribute to the calculated pacing rate value; and
  MAX_COUNT is a counter value that determines the length of the required pre-step response at-rest period.

Preferably, the DIPSIZE, DIPSLOPE, STPCRIT, STEP_SIZE, STEP_SLOPE, STEP_DURATION, STPCRTR and MAX_STEP_RATE, and MAX_COUNT parameters are all initially input by a physician or programmer. Typical values for the various criteria and step rate response parameters are:
  DIPSIZE=0.16 degrees C.;
  DIPSLOPE=0.06 degrees C./differential cycle;
  STPCRTR=80 beats per minute;
  STPCRI=0.04 degrees C.;
  STEP_SIZE=15 beats per minute;
  STEP_DURATION=4 differential cycles, which is equivalent to 32 pacer cycles in the presently preferred embodiment;
  MAX_STEP_RATE=85 beats per minute; and
  MAX_COUNT=2 differential cycles.

The meanings of differential cycle and rate calculation cycle, and their relation to the pacer cycle are described in detail below with respect to a preferred implementation of the rate algorithm.

The first criteria term (TVG−DYNRFT)<STPCRIT prevents the activation of the step response when the temperature differential indicates an exercise response is already underway. As described previously, the term (TAVG−DYNRFT) increases as TAVG rises with exercise and decreases as TAVG falls and DYNRFT increases after exercise is stopped. Thus, this temperature difference term provides an indication whether the sensed dip is due to the initial onset of exercise or is perhaps due to a momentary dip during an already existing exercise response or to the termination of exercise.

The second criteria is a counter T_CTR associated with the first criteria term. The counter T_CTR is initially given a value of MAX_COUNT. Each time the first criteria is tested and satisfied, T_CTR is tested and decremented if it is greater than zero. If the first criteria is not satisfied at any time, T_CTR is reset to MAX_COUNT. The remainder of the step criteria are only tested if T_CTR equals zero. Thus, the T_CTR criteria ensures that a patient has been at rest for at least MAX_COUNT consecutive differential cycles immediately preceding the activation of a step response. For example, at 70 beats per minute with a differential cycle occurring every 32 pacer cycles, a 10 minute at-rest period corresponds to a preferred MAX_COUNT value of approximately 22 differential cycles.

The third criteria term (TL−TAVG) provides an indication of short term negative temperature trends. As described in detail below, each differential cycle, which in the presently preferred embodiment corresponds to 32 pacer cycles, the current average temperature TAVG is stored as TL for use in the next differential cycle. Thus, the third criteria term provides an indication of the sharpness of the drop in average temperature between successive differential cycles. The third dip criteria is met when the drop in average temperature between successive differential cycles exceeds DIPSLOPE.

The fourth criteria term (TPEAK−TAVG) also provides an indication of negative temperature trends. As TAVG increases, TPEAK remains equal to TAVG and the difference between the two elements remains at zero. As TAVG drops, TPEAK remains at the highest value of TAVG previously sensed and the difference increases as TAVG continues to drop until at some point the DIPSIZE criteria is met.

The fifth criteria term RATE<STPCRTR ensures that a step response is not added when the calculated pacing rate is already at an elevated value indicating that an exercise response is already underway. As illustrated in FIG. 3, actual temperature response is not as smooth as illustrated in the smoothed graph of FIG. 4. Instead there are peaks and valleys associated with the response even when the overall trend is rising in response to exercise. Thus, the third criteria ensures that such a momentary dip in temperature occurring during an exercise response will not alone activate a step response.

Even if the sensed dip satisfies all five criteria, it is preferred that the overall pacing rate not exceed a maximum value MAX_STEP_RATE with the addition of the step rate adjustment. Thus, if the pacing rate is already greater than MAX_STEP_RATE, no step response is added even if the other criteria are met. If the pacing rate is less than MAX_STEP_RATE but addition of the step response would cause the overall pacing rate to exceed MAX_STEP_RATE, then the overall pacing rate is limited to MAX_STEP_RATE.

Assuming that a sensed dip in blood temperature satisfies all five criteria and a step response is added to the calculated pacing rate value, at some predetermined point after the step response is activated it is assumed that the dynamic rate response term is providing sufficient rate response so that the additional rate response of the step rate response term is no longer needed. At this point, the step rate response is allowed to gradually decay until it no longer contributes to the calculated pacing rate value.

Figure 7:
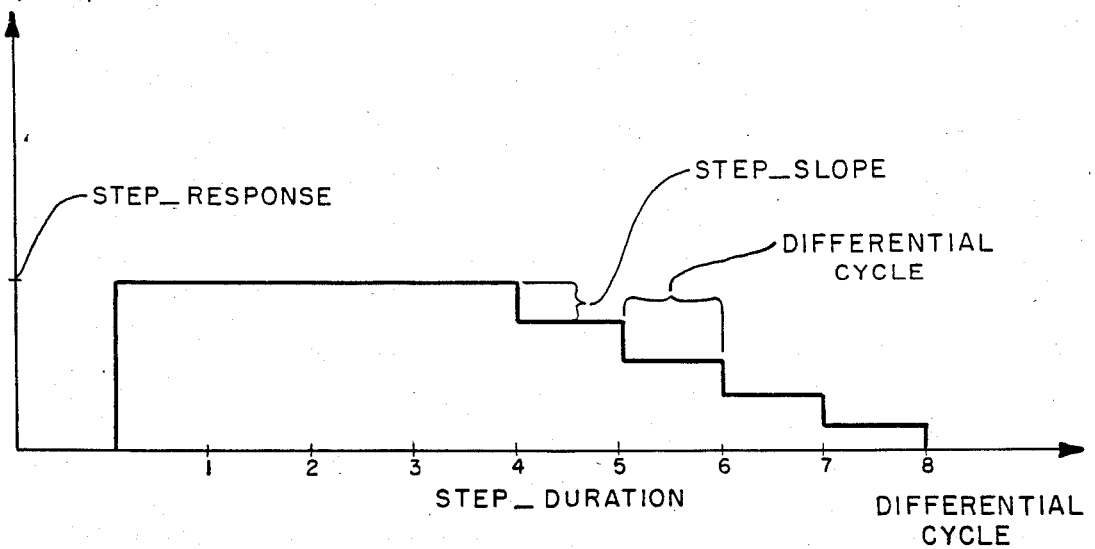
FIG. 7 is a graphical representation of the step rate response function of the preferred rate algorithm of the temperature responsive controller.

The point at which the step rate response begins to decay is set by STEP_DURATION. In the presently preferred embodiment, STEP_DURATION is equal to four differential cycles after the step response STEP_RESPONSE is first applied. After the duration determined by STEP_DURATION, the step response is reduced each succeeding differential cycle by the value of the parameter STEP_SLOPE until it no longer contributes to the calculated pacing rate value. In the preferred embodiment, STEP$_{13}$ SLOPE is equal to four beats per minute. Accordingly, in the preferred embodiment, the step response term contributes additional rate equal to STEP_RESPONSE for four differential cycles, and then decays until it contributes nothing after four additional differential cycles as shown in FIG. 7.

In addition to the rate response calculation features described thus far, the preferred rate response algorithm also includes features designed to enhance the safety and accuracy of the inventive controller. These features are described generally here and their detailed operation is described below in conjunction with the detailed description of a presently preferred implementation of the rate algorithm.

One such feature is slew rate control. The slew rate control feature limits the amount by which the calculated pacing rate is allowed to change between successive rate calculation cycles. Each time a new rate calculation is made, the magnitude of the difference between the currently calculated rate RATE and the rate calculated the previous rate calculation cycle LAST_RATE is determined. If the difference exceeds a maximum slew rate value MAX_SLEW_RATE then the amount of change is limited to MAX_SLEW_RATE. In the presently preferred rate algorithm, MAX_SLEW_RATE is equal to 2 beats per minute per calculation cycle. The value of MAX_SLEW_RATE is initially input by a physician or programmer as described above.

It should be apparent that the slew rate control feature also limits the amount of rate contributed by the step rate response term during each rate calculation cycle. For example, if STEP_RESPONSE is 15 beats per minute and MAX_SLEW_RATE is 2 beats per minute per calculation cycle, it will take 8 calculation cycles (i.e. one differential cycle) of the preferred rate algorithm for the rate contributed by the step response term to have its full effect on the calculated pacing rate value.

Another feature is saturation detection and control. Rate saturation can occur when the parameters of the rate response algorithm are selected such that the calculated pacing rate can exceed the desired maximum rate limit when the patient is exercising and his temperature is increasing. In such case, even though the calculated pacing rate is limited to the maximum rate limit, the pacing output unit 40 will continue to generate pulses at the maximum rate for a period of time after the patient has discontinued physical activity until the difference between TAVG and DYNRFT drops sufficiently for the calculated pacing rate to drop below the desired maximum rate limit.

Figure 8:
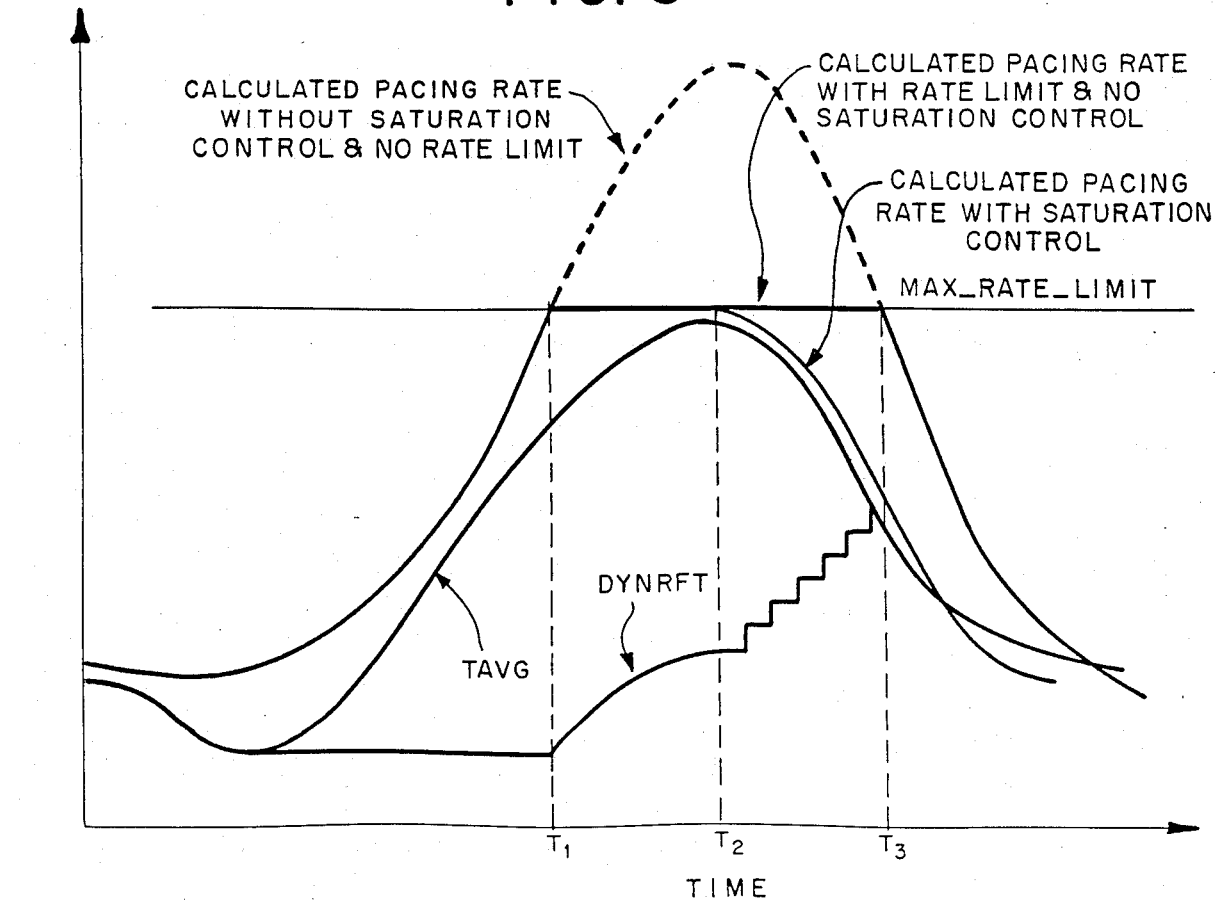
FIG. 8 is a graphical representation of a typical calculated pacing rate illustrating the operation and effect of the saturation control feature of the preferred rate response algorithm of the temperature responsive controller.

FIG. 8 illustrates how the preferred rate algorithm detects and controls maximum pacing rate and rate saturation using the previously described dynamic reference temperature variable DYNRFT. FIG. 8, like FIG. 4, is somewhat exaggerated and smoothed to facilitate discussion and illustration of the involved rate parameters.

As the patient exercises, both the average blood temperature TAVG and the pacing rate calculated by the rate response algorithm rise. At some point in time, the calculated pacing rate may exceed the value of a parameter designated MAX_RATE_LIMIT which is initially input by a physician or programmer. In the preferred rate algorithm, MAX_RATE_LIMIT is equal to approximately 133 beats per minute. When the calculated pacing rate exceeds MAX_RATE_LIMIT, a rate saturation condition exists. FIG. 8 illustrates that even if the o calculated pacing rate is limited to MAX_RATE_LIMIT, if saturation is not controlled, the pacing output unit 40 will continue to pace the heart at the maximum rate for some time after exercise has been discontinued and the average blood temperature has begun to fall.

In order to eliminate this undesirable condition, each time the rate algorithm calculates a new TAVG, it also stores TAVG from the last rate calculation cycle as TNL. Then for each rate calculation cycle during which the calculated pacing rate equals or exceeds MAX_RATE_LIMIT and TAVG is increasing, the algorithm adjusts DYNRFT upwardly by the same amount as the increase in TAVG as follows:

$$DYNRFT = DYNRFT + (TAVG - TNL).$$

It should be apparent that so long as DYNRFT increases in the same amount as TAVG, the dynamic rate response term, which is a function of (TAVG−DYNRFT), does not contribute additional rate to the calculated pacing rate value even though TAVG continues to rise. Even though additional rate response is still contributed to the calculated pacing rate by the natural rate response term, the contribution is minimal.

When the physical activity stops and TAVG ceases rising and begins to fall, the rampback criteria RBCRIT is satisfied and DYNRFT begins to adjust upwardly in the manner previously described. As a result, the rate contributed by the dynamic rate response also decreases. Since the calculated pacing rate was limited to MAX_RATE_LIMIT, the drop in the dynamic rate response causes the calculated pacing rate to immediately fall below the maximum rate limit of the pacing output unit 40.

Figure 9A:
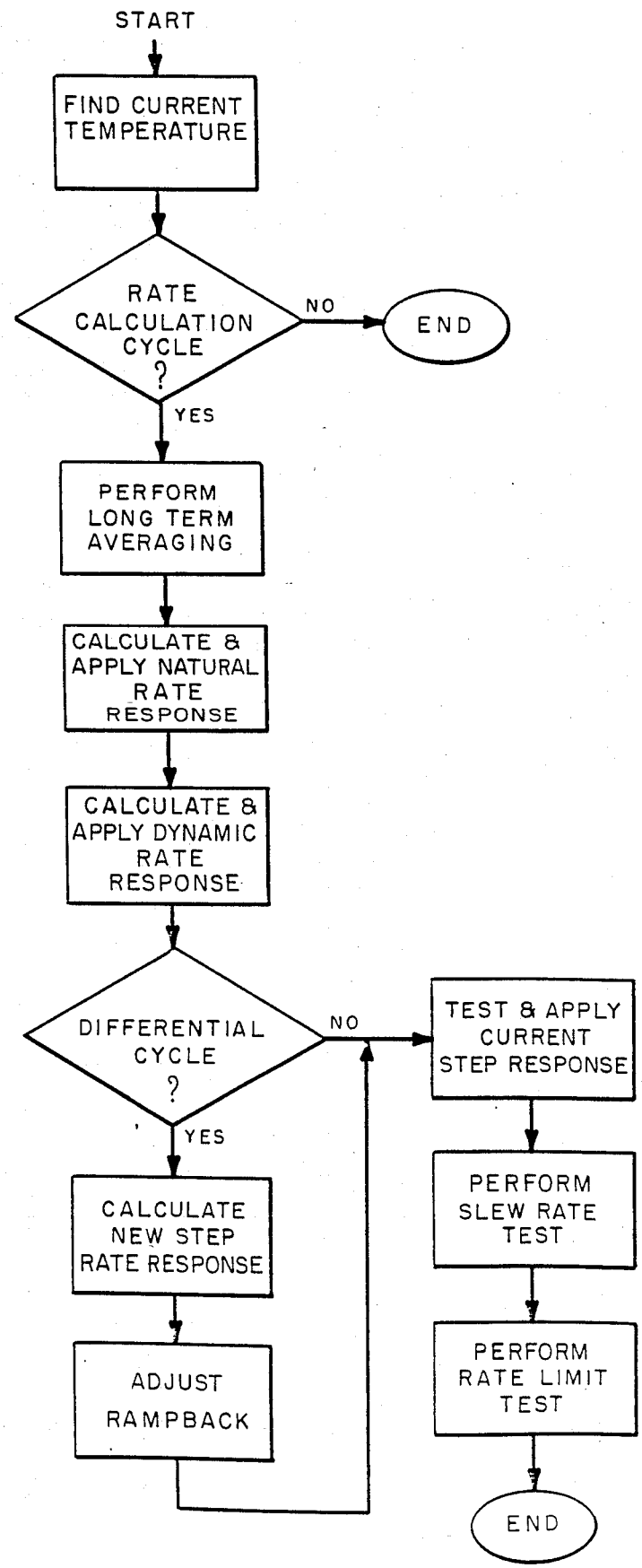
FIG. 9a is a flow chart illustrating generally the operation of a preferred implementation of the rate response algorithm.

FIGS. 9a–g illustrate the operation of the presently preferred rate algorithm. FIG. 9a in particular illustrates an overview of the operation of the entire rate algorithm. Each time the algorithm is entered, it first finds and stores the current temperature. It next determines whether it is in a rate calculation cycle. If it is not, it ends without updating the current calculated pacing rate. However, if it is in a rate calculation cycle, it performs the long term temperature averaging calculation and updates REFTMP. It then calculates the natural and dynamic rate responses and applies them to the calculated pacing rate value. Next, it determines whether it is in a differential cycle. If it is not, it proceeds to apply the current step response, if activated and appropriate, to the calculated pacing rate value. Having completed calculation of the new pacing rate, it then performs the slew rate test to determine whether any calculated rate change is within acceptable limits, performs the rate limit and saturation control functions, stores the new and old pacing rates, and ends. If the algorithm is in a differential cycle, it first tests the step criteria. If they are all satisfied, it activates a new step response. Next it determines if a rampback adjustment of the dynamic reference temperature is required and, if so, makes the appropriate adjustment. It then proceeds to apply the step response, if any, to the calculated pacing rate value, performs the slew rate test, performs the rate limit and saturation control functions, stores the new and old pacing rates, and ends.

Figure 9B:
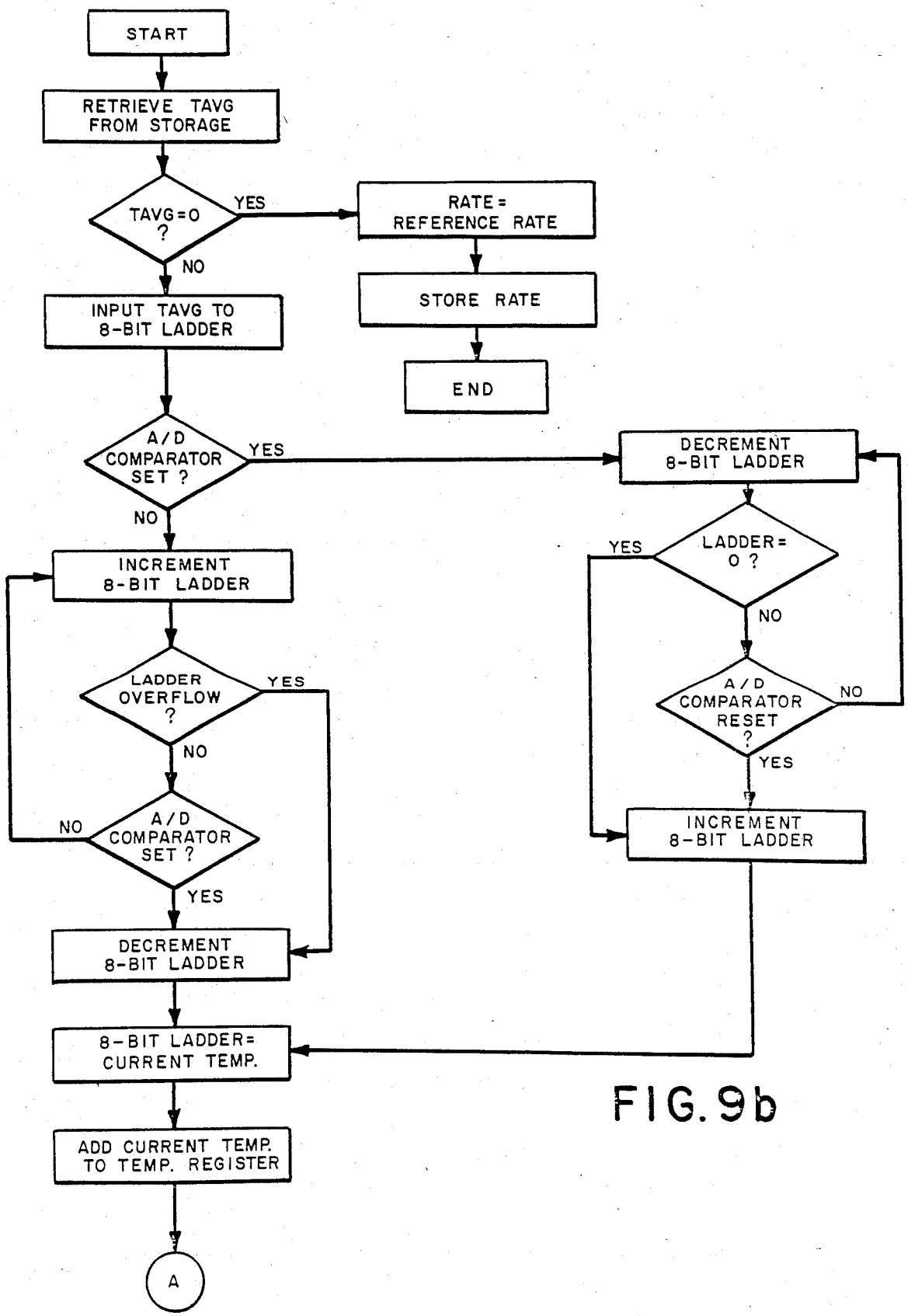
FIG. 9b is a flow chart illustrating the detailed operation of the rate response algorithm in finding the current temperature.

FIG. 9b illustrates the detailed operation of the rate algorithm in finding the current temperature. Each time the algorithm is entered, it retrieves the average temperature (TAVG) from memory 30. If TAVG equals zero then the temperature rate response is disabled. The algorithm sets the rate to the reference rate, stores the rate, and ends.

If TAVG is not zero, it is loaded into the 8-bit ladder and the output 64 of the comparator 90 is tested. If the output is not set, indicating that the 8-bit input is less than the current temperature, the 8-bit value is incremented and checked for an overflow condition. If there is no overflow, the comparator output is again tested. When a state change is detected, the algorithm decrements the 8-bit value and adds it to the contents of a temperature register. If the 8-bit value overflows before the comparator output changes state, the algorithm decrements the 8-bit value and adds it to the temperature register.

If the output is initially set, indicating that the 8-bit input value is greater than the current temperature, then the 8-bit value is decremented and tested for a zero condition. If the value is not zero, the comparator output is tested for a state change. The algorithm continues to decrement the 8-bit value and test the comparator output until a state change is detected. It then increments the 8-bit value and adds it to the temperature register. However, if the 8-bit value goes to zero before a state change is detected, the algorithm increments the 8-bit value and adds it to the contents of the temperature register.

Figure 9C:
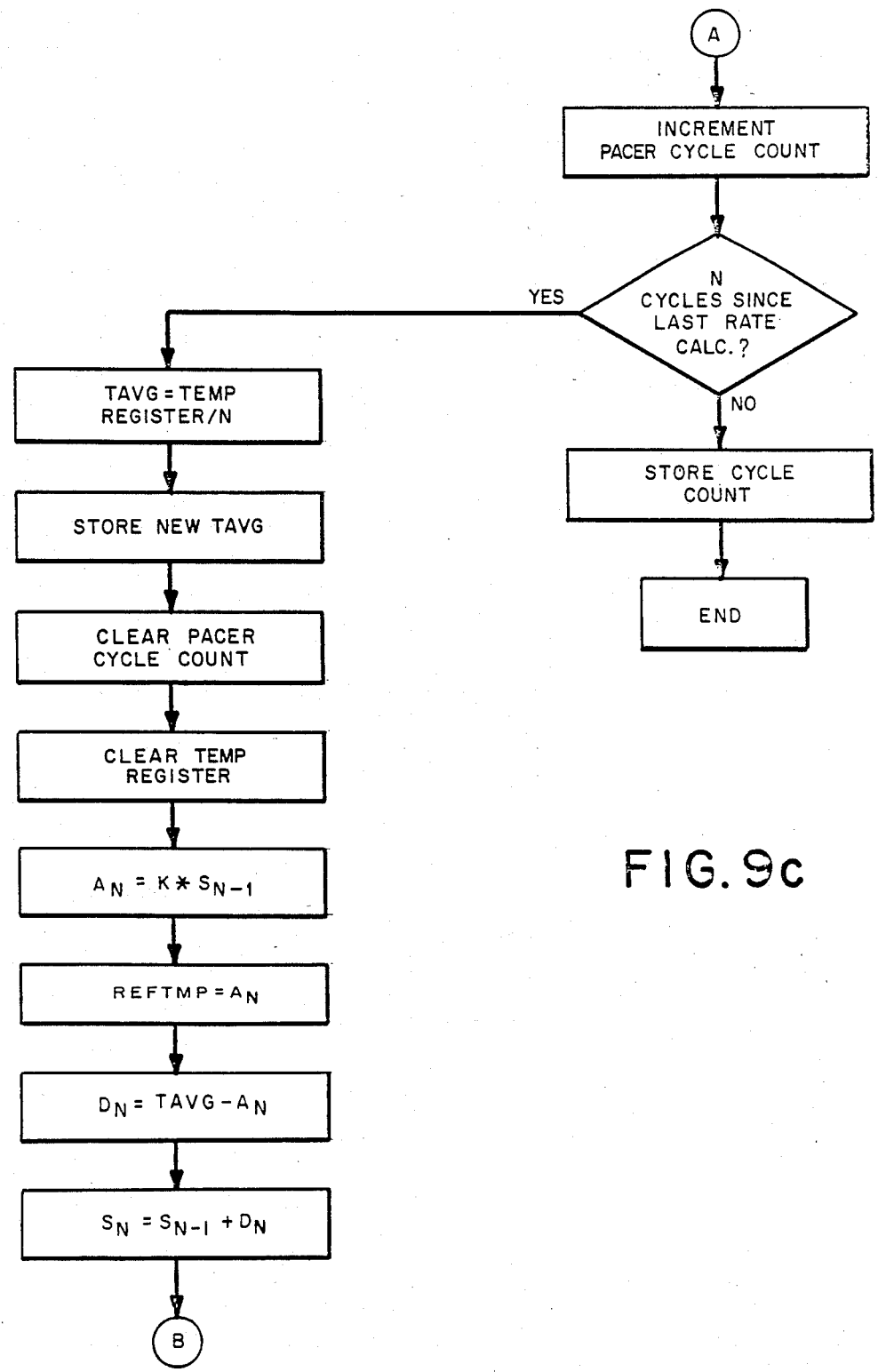
FIG. 9c is a flow chart illustrating the detailed operation of the rate response algorithm in performing a long term reference temperature averaging function.

FIG. 9c illustrates the detailed operation of the rate algorithm in determining whether it is in a rate calculation cycle and in adjusting the reference temperature after it has found the current temperature. At this stage, the algorithm increments a pacer cycle count variable. If the variable indicates that less than N pacer cycles have been counted, the algorithm stores the new cycle count in memory 30 and ends without calculating a new pacing rate. However, if N cycles have been counted, the algorithm proceeds to calculate a new TAVG. The algorithm divides the value in the temperature register by N to obtain the new TAVG, stores the new TAVG, and clears the pacer cycle count and the temperature register. In the preferred embodiment N=4 and a new TAVG and new pacing rate are calculated every four pacer cycles, which at a pacing rate of 70 beats per minute, is approximately every 3.4 seconds. It is understood that a temperature reading is taken every pacer cycle, however.

The algorithm next performs the long term averaging calculation and updates the reference temperature REFTMP. First the algorithm calculates the weighted average temperature $A_N = K^* S_N - 1$. Next the algorithm determines the deviation $D_N$ between TAVG and the weighted average temperature $A_N$ and calculates the new weighted sum $S_N$ for use in the next REFTMP recalculation.

Figure 9D:
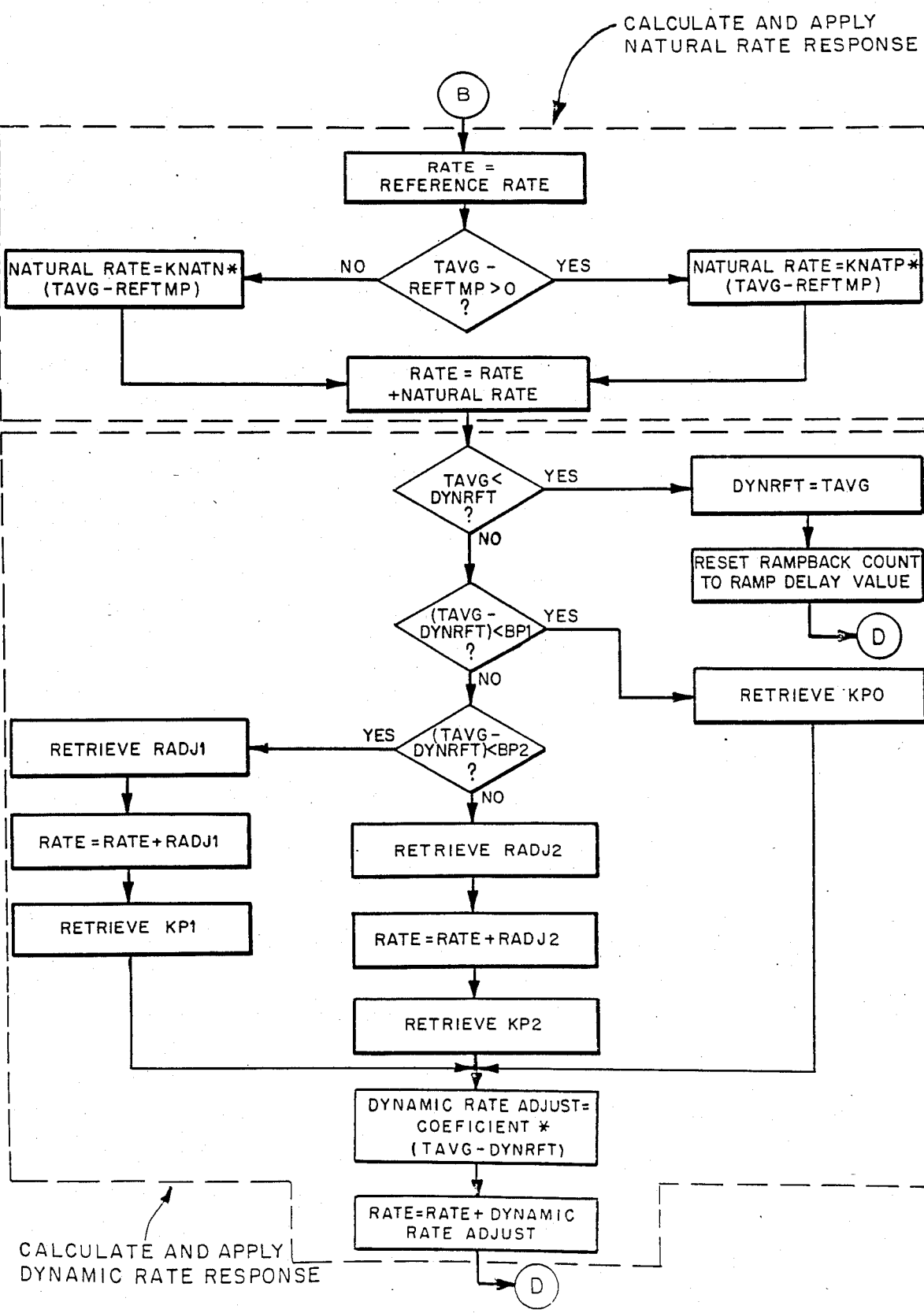
FIG. 9d is a flow chart illustrating the detailed operation of the rate response algorithm in calculating and applying natural and dynamic rate response terms.

As illustrated in FIG. 9d, the algorithm next proceeds to calculate a new pacing rate. Initially the algorithm sets the pacing rate to the reference rate. Next it calculates the natural rate response. If TAVG is greater than REFTMP, the algorithm calculates the natural rate response as KNATP*(TAVG−REFTMP). If TAVG is less than REFTMP, the algorithm calculates the natural rate response as KNATN*(TAVG−REFTMP). The algorithm then adds the natural rate response to the calculated pacing rate.

Next the algorithm adjusts the dynamic reference temperature and calculates the dynamic rate response. If TAVG is less than DYNRFT, the algorithm sets DYNRFT equal to TAVG and resets a ramp back count variable to the value of the RAMP DELAY parameter previously described. Thus, DYNRFT is never allowed to be greater than TAVG. The algorithm then goes on to determine if it is in a differential cycle as described below.

However, if TAVG is greater than DYNRFT, the algorithm determines whether the temperature differential is less than BP1. If it is, the algorithm retrieves the coefficient KP0 corresponding to the first segment of the dynamic rate response function from memory 30. If it is not, the algorithm goes on to determine whether the differential is less than the second break point BP2. If it is, the algorithm retrieves the constant RADJ1 from memory 30 and adds it to the rate. It then retrieves the coefficient KP1 corresponding to the second segment of the dynamic rate response function from memory 30. If the differential is greater than the breakpoint BP2, the algorithm retrieves the constant RADJ2 from memory 30 and adds it to the rate. It then retrieves the coefficient KP2 corresponding to the third segment of the dynamic rate response function from memory 30. The algorithm then completes the dynamic rate response adjustment to the pacing rate. It calculates the dynamic rate adjustment as the selected coefficient*(TAVG−DYNRFT), and adds the dynamic rate adjustment to the pacing rate.

Figure 9E:
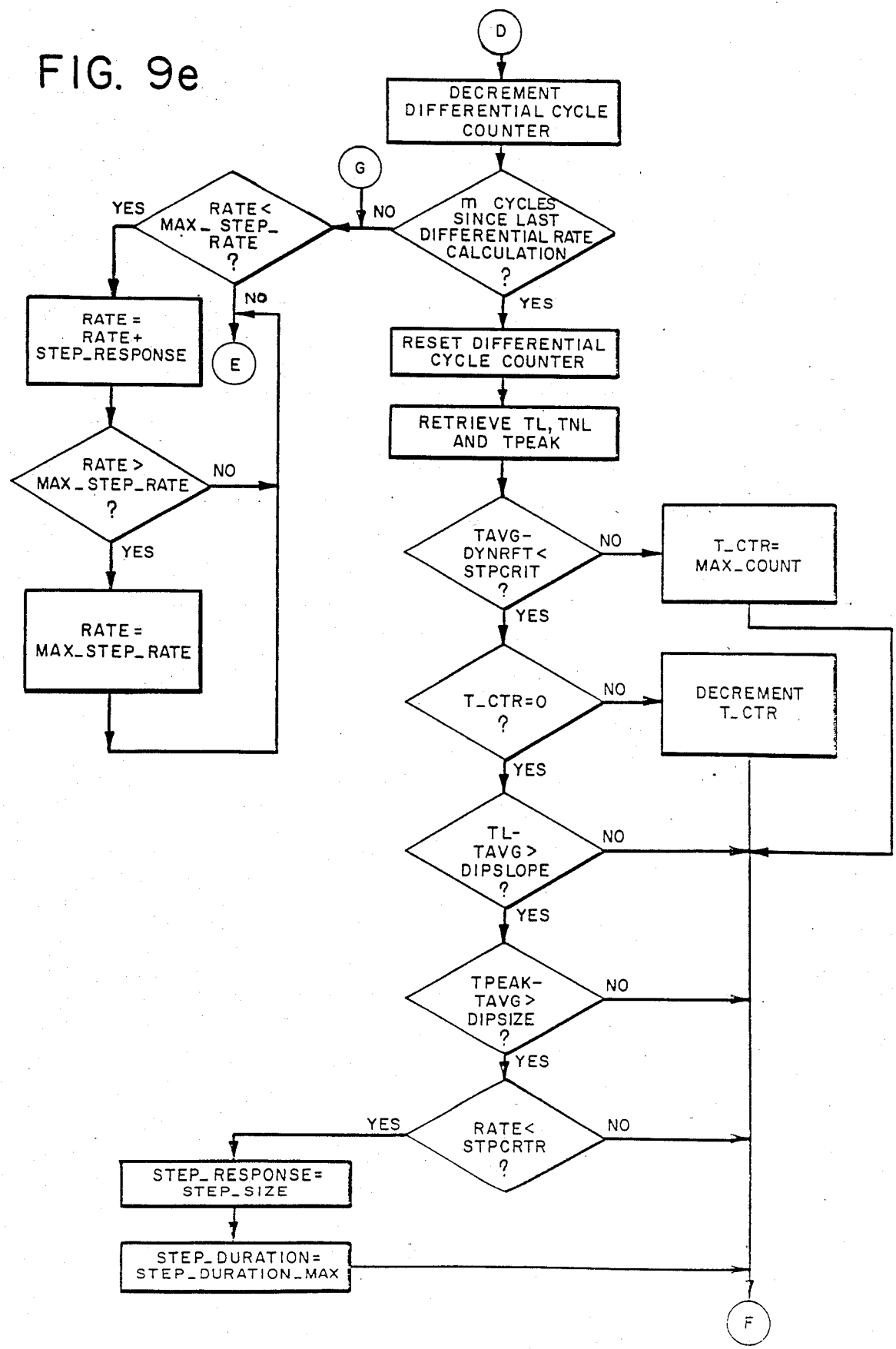
FIG. 9e is a flow chart illustrating the detailed operation of the rate response algorithm in calculating and applying a step rate response term.
Figure 9F:
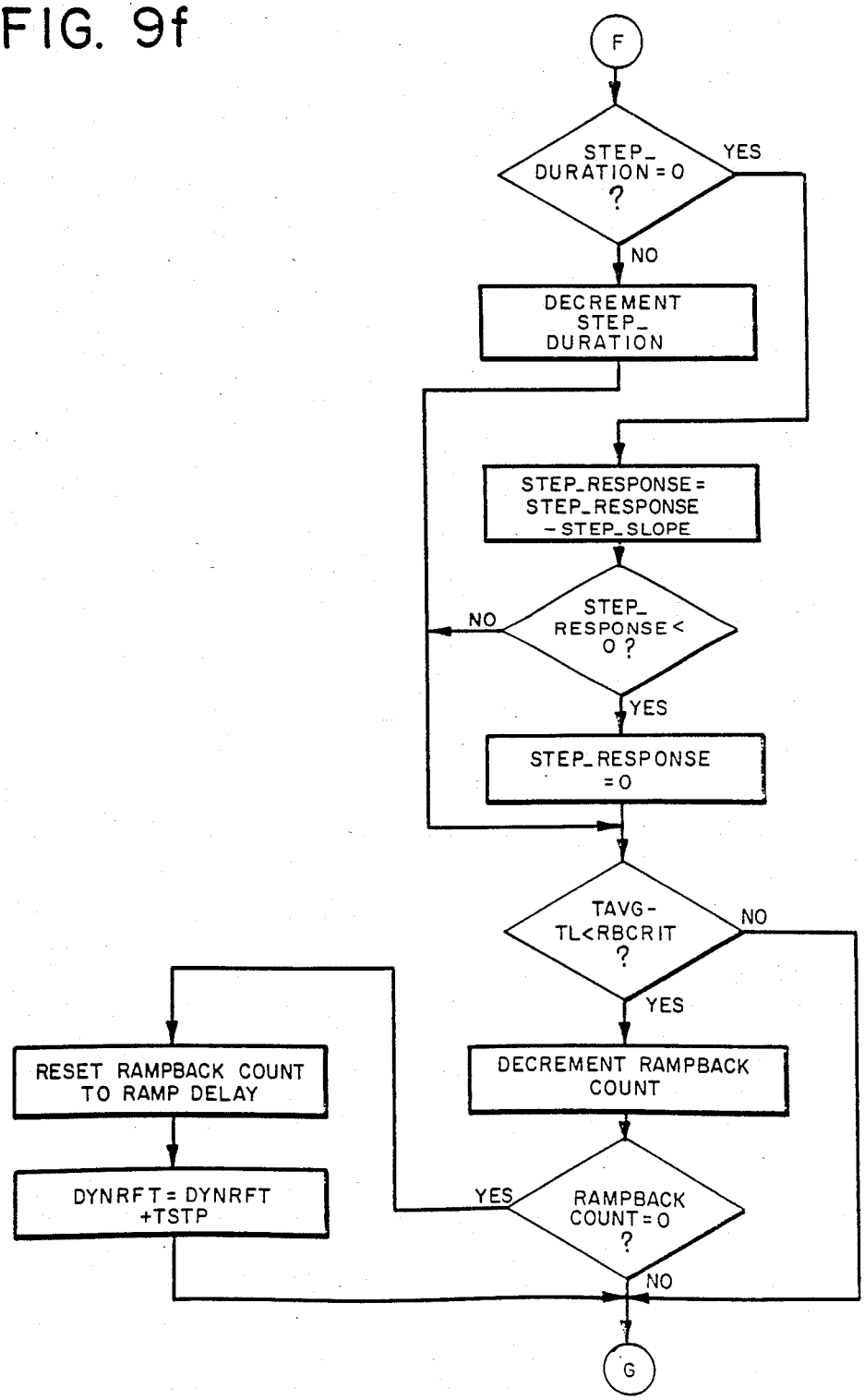
FIG. 9f is a flow chart illustrating the detailed operation of the rate response algorithm in updating various step rate response parameters and performing rampback adjustment.
Figure 9G:
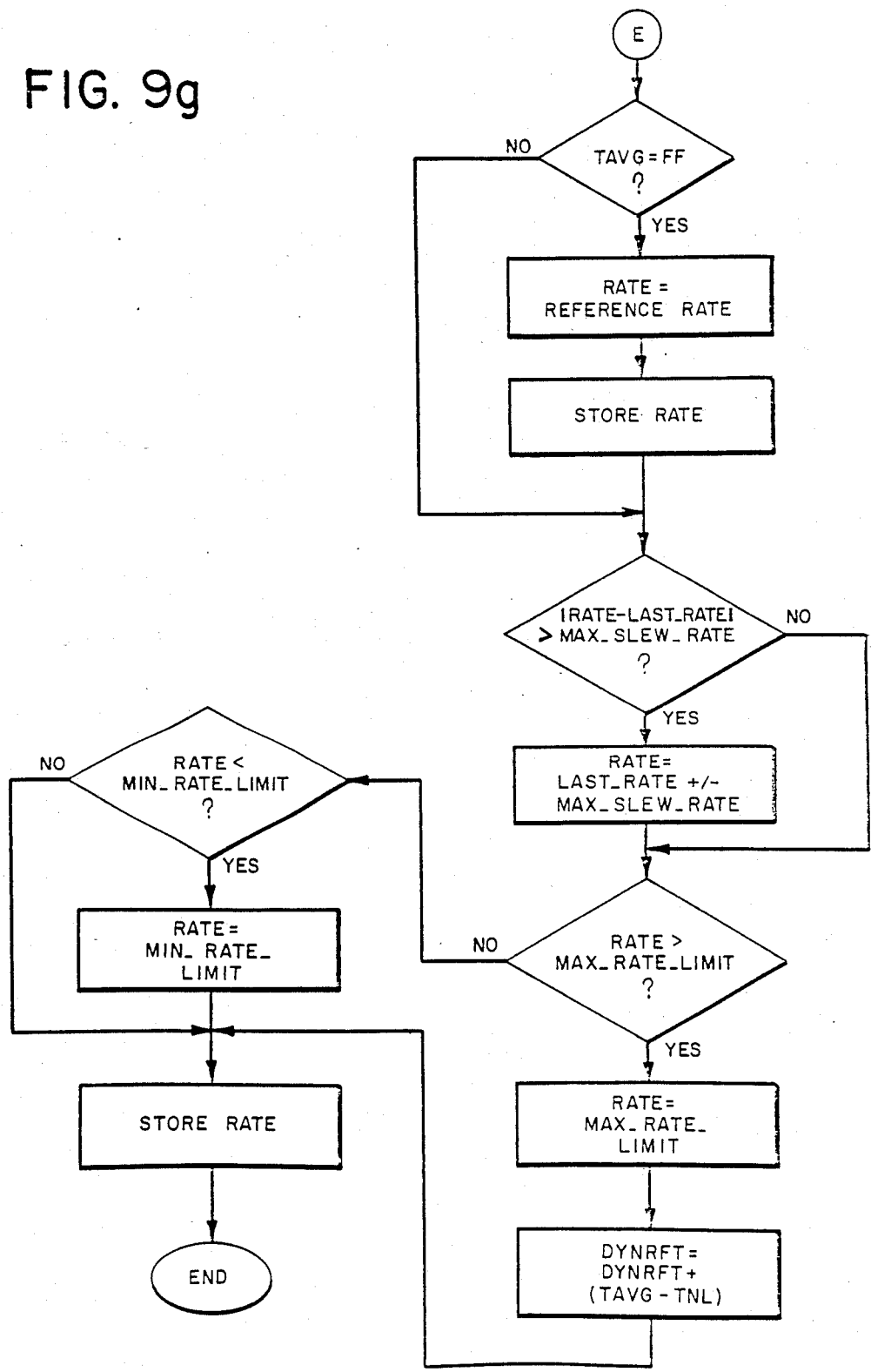
FIG. 9g is a flow chart illustrating the detailed operation of the rate response algorithm performing slew rate, saturation control, and rate limit functions.

As illustrated in FIG. 9e, the algorithm next determines whether it is in a differential cycle. If it is, it tests the step criteria and activates and applies the new step response, if appropriate. As illustrated in FIG. 9f, it then updates the step response parameters and performs the DYNRFT rampback adjustment. As shown in FIG. 9g, it then performs the slew rate, rate limit, and saturation functions before storing the new and old pacing rates and ending. If it is not in a differential cycle, it applies the current step response, if appropriate, performs the slew rate, rate limit and saturation functions, and then ends after storing the new and old pacing rates.

With reference to FIG. 9e, the algorithm decrements a differential cycle counter to determine whether it is in a differential cycle. The preferred initial value M for the counter is 8. Accordingly, in conjunction with the preferred value for N of 4, a differential cycle occurs every M=8 rate calculation cycles or every M * N=32 pacer cycles. At a pacing rate of 70 beats per minute, for example, a differential cycle occurs approximately every 27.4 seconds.

If the cycle counter is not zero, the algorithm is not in a differential cycle. Accordingly, it first determines whether it is appropriate to apply the current step response to the calculated pacing rate. If the current calculated pacing rate is greater than MAX_STEP_RATE, the algorithm does not apply the step response but goes on to perform the slew rate test and other functions described below. If, however, the current calculated pacing rate is less than MAX_STEP_RATE, the algorithm proceeds to apply the step response, if any. The algorithm adds STEP_RESPONSE to the pacing rate and then checks to see if the new pacing rate exceeds MAX_STEP_RATE. If so, it sets the pacing rate equal to MAX_STEP_RATE before proceeding to the slew rate test section.

If the value of the differential cycle counter indicates that the algorithm is in a differential cycle, the algorithm first resets the counter to M, and retrieves the variables TL, TNL and TPEAK for use in the differential calculations. The algorithm then tests the five step response criteria to determine whether a new step response should be activated.

It first determines whether TAVG−DYNRFT is less than STPCRIT. If not, it resets T_CTR to MAX_COUNT and updates the step response parameters STEP_RESPONSE and STEP_DURATION before proceeding to the rampback section described below. Referring to FIG. 9f, STEP_DURATION is adjusted by decrementing it if it is not already equal to zero. If STEP_DURATION is equal to zero, then STEP_RESPONSE is decremented by the value of STEP SLOPE. STEP_RESPONSE is reset to zero if it is less than zero.

If TAVG−DYNRFT is less than STPCRIT, the algorithm checks T_CTR. If T_CTR is not equal to zero, it is decremented and the STEP_RESPONSE and STEP_DURATION parameters are updated as described above before the algorithm proceeds to the rampback section. If T_CTR does not equal zero, the algorithm proceeds to test each of the remaining criteria. If any one of the criteria is not satisfied, the algorithm updates the STEP_RESPONSE and STEP_DURATION parameters and proceeds to the rampback section. If, however, all of the criteria are satisfied, the algorithm activates a new step response by resetting STEP_RESPONSE equal to STEP_SIZE and STEP_DURATION equal to STEP_DURATION_MAX before updating the parameters and proceeding to the rampback section.

As illustrated in FIG. 9f, the rate algorithm determines whether rampback adjustment is required by determining whether the average temperature differential (TAVG−TL) is less than the rampback criteria parameter RBCRIT. It will be recalled that TAVG is the current average temperature and TL is the average temperature at the previous differential cycle. If the differential is less than RBCRIT, the algorithm decrements the rampback count, which it initially set to the value of the RAMP DELAY parameter. If the rampback count is now zero, the algorithm resets the rampback count to the value of RAMP DELAY and increments DYNRFT by the value of the step parameter TSTP previously described. It should be apparent that the time delay between increments of DYNRFT in the preferred algorithm is calculated as 32 pacer cycles per differential calculation * 60 seconds per minute * the value of RAMP DELAY divided by the number of pacer cycles per minute. For example with a RAMP DELAY value of four and a pacing rate of 70 beats per minute, the delay between each DYNRFT increment is approximately 109.7 seconds.

After completing the rampback adjustment operation, the rate algorithm proceeds to apply the new step rate response, if any and if appropriate, as described above with reference to FIG. 9e. The algorithm enters the flow of operation illustrated in FIG. 9e at point "G".

After the step rate response, if any, is applied, the rate algorithm proceeds to the slew rate test and rate limit sections. With reference to FIG. 9g, the algorithm first determines if the measured temperature is at the ladder 72 maximum value of FFH. If so, the algorithm sets the pacing rate to the reference rate and stores the new rate before performing the slew rate test. The algorithm performs the slew rate test by determining whether the absolute value of the difference between the current calculated pacing rate and the previous calculated pacing rate exceeds MAX_SLEW_RATE. If it does, then the algorithm limits the new pacing rate to the pacing previous rate ± the MAX_SLEW_RATE depending on whether the new calculated pacing rate is greater than or less than the previous rate.

The rate algorithm then performs the rate limit and saturation control functions. It first determines if the calculated pacing rate is greater than MAX_RATE_LIMIT or less than MIN_RATE_LIMIT. If either case is true, it limits the calculated pacing rate to the appropriate value. In addition, if the calculated pacing rate exceeds MAX_RATE_LIMIT, the algorithm prevents rate saturation from occurring by adjusting DYNRFT up by (TAVG−TNL), the increase in average temperature over the previous rate calculation cycle. After the algorithm completes the rate limit and saturation control functions, it stores the new pacing rate, stores the previous pacing rate as LAST_RATE, and ends.

What have been described are various aspects of a temperature responsive pacer controller which constitute presently preferred embodiments of the invention. It should be apparent that the foregoing description and accompanying illustration is merely exemplary of certain features of the invention and is in no way intended to be limiting. Various changes and modifications to the preferred embodiments will be apparent to those skilled in the art. For example, various adjustments to the rate response functions, temperature ranges, parameter values, algorithm operation and the like may be made. In addition, various modifications to the calculated pacing rate may be made, for example splitting the calculated pacing rate value into two complementary values corresponding to A-V and V-A delay for use in a dual chamber sensing and pacing arrangement. Such changes and modifications as well as others can be made without departing from the spirit and scope of the invention. Accordingly, it is intended that all such changes and modifications be covered by the following claims and their equivalents.

We claim:

1. A cardiac pacemaker adapted to vary its pacing rate according to the physiological state of the pacemaker patient, comprising:

means for detecting the patient's central venous blood temperature; and means responsive to the detected blood temperature for adjusting the pacing rate according to predetermined relationships between blood temperature and desired heart rate including non-exercise related and exercise related terms that depend upon variations in the blood temperature relative to a respective reference temperature, said adjusting means including means for determining a moving dynamic reference temperature that establishes a moving temperature reference value from which to measure the current change in blood temperature indicative of the metabolic need and means to adequately adjust the pacing rate accordingly.

2. The pacemaker of claim 1 wherein said means for determining said moving dynamic reference temperature comprises:
means for calculating said moving dynamic reference temperature as a value which is movable relative to the value of said detected blood temperature according to whether said detected blood temperature is changing at a rate greater than or less than a predetermined rate of change indicative of a predetermined level of exercise.

3. The pacemaker of claim 2 wherein said calculating means calculates a rapid decrease of the value of said moving dynamic reference temperature to the value of said detected blood temperature whenever said detected blood temperature falls below the moving dynamic reference temperature, whereby to avoid any contribution of said exercise related term to the adjustment of pacing rate during periods of non-exercise by the patient.

4. The pacemaker of claim 2 wherein said calculating means calculates a gradual increase of the value of said moving dynamic reference temperature toward the value of said detected blood temperature whenever said detected blood temperature is changing at a rate less than said predetermined rate of change, whereby to gradually reduce the relative contribution of the exercise related term to the adjustment of pacing rate upon cessation of exercises by the patient.

5. The pacemaker of claim 4 wherein said calculating means calculates the gradual increase of the value of said moving dynamic reference temperature in a stepwise manner.

6. The pacemaker of claim 1, further comprising means to limit the rate of change of said pacing rate during the adjustment thereof.

7. The pacemaker of claim 1, further comprising means to maintain the adjusted pacing rate within selected maximum and minimum rate limits.

8. The pacemaker of claim 7, further comprising means to prevent the adjusted pacing rate from remaining at said maximum rate limit after cessation of exercise by the patient.

9. A cardiac pacemaker having a stimulation rate which is adjusted according to variations of the blood temperature of the patient, comprising:
means for measuring the blood temperature;
means responsive to measurement of the blood temperature to detect a drop thereof for determining whether said detected temperature drop is indicative of the onset of exercise by the patient, said determining means being adapted to make said determination by applying criteria from the group consisting of (i) the relative difference between the value of the detected blood temperature and the value of a predetermined reference temperature, (ii) whether said relative difference has been less than a preselected value over a predetermined interval, (iii) the magnitude of the detected temperature drop, (iv) the rate of variation of the detected temperature drop, and (v) the present stimulation rate relative to a preselected reference rate; and
means responsive to a determination that the detected temperature drop is indicative of the onset of exercise for generating a stepped up stimulation rate.

10. The pacemaker of claim 9, wherein said means for determining initially determines whether said relative difference has been less than said preselected value over said interval, and then tests the other criteria only if that criterion is satisfied.

11. The pacemaker of claim 9, further comprising means responsive to the level of the stepped up stimulation rate relative to a preselected maximum stimulation rate for limiting said stepped up rate not to exceed said preselected maximum rate.

12. The pacemaker of claim 9, further comprising means responsive to variations in the measured blood temperature commensurate with exercise by the patient for calculating a smoothly varying stimulation rate, and means for gradually reducing said stepped up rate after a selected interval in favor of adjustment of stimulation rate according to said calculated rate.

13. A stimulus generator for variably controlling the stimulation rate of a cardiac pacer according to variations of the patient's blood temperature, comprising:
means for sensing the blood temperature;
means for determining a moving dynamic variable reference temperature having an instantaneous value related to variations of the sensed blood temperature relative to a preselected rate of variation of the blood temperature;
means responsive to the sensed blood temperature and to the relative value of the determined dynamic reference temperature for calculating a dynamic hear rate response related to variations in said sensed blood temperature relative to said dynamic reference temperature attributable to exercise by the patient; and
means for combining said dynamic heart rate response with a predetermined bas rate to obtain a desired stimulation rate for said stimulus generator.

14. The stimulus generator of claim 13, further comprising:
means for establishing a relatively static reference temperature;
means responsive to the sensed blood temperature and to said static reference temperature for calculating a natural heart rate response related to non-exercise related variations in said sensed blood temperature relative to said static reference temperature; and
means for combining said natural heart rate response with said dynamic heart rate response and said base rate to obtain said desired stimulation rate.

15. The stimulus generator of claim 14 wherein said establishing means includes means for periodically recalculating said static reference temperature as a long-term weighted average temperature over a selectable interval.

16. The stimulus generator of claim 13, further comprising:
means responsive to a variation of the sensed blood temperature indicative of the onset of exercise by the patient for calculating a step rate response; and means for combining said step rate response with said dynamic rate response and said base rate to obtain said desired stimulation rate.

17. The stimulus generator of claim 16 wherein said step rate response calculating means comprises means for testing selected criteria related to the magnitude and slope of downward variations in said blood temperature to determine whether any such variation is indicative of the onset of exercise.

18. The stimulus generator of claim 17 wherein said testing means further tests selected criteria related to the present stimulation rate and to the relative difference between said blood temperature and said dynamic reference temperature during a predetermined interval preceding the calculation of said step response.

19. The stimulus generator of claim 13 wherein said means for sensing blood temperature comprises:
  thermistor means for generating an analog signal indicative of said blood temperature; and
  analog-to-digital converter means for converting each value of said generated analog signal to a respective digital value.

20. The stimulus generator of claim 19 wherein said converter means further comprises:
  input means for detecting a digital value; and
  comparator means for comparing the detected digital value with said generated analog signal and providing an indication of correspondence therebetweeen.

21. The stimulus generator of claim 20 wherein said converter means further comprises adjustment means for selectively altering the correspondence between digital values and analog signals.

22. The stimulus generator of claim 13, further comprising means to limit the rate of change of the stimulation rate while combining the responses to obtain a desired rate.

23. The stimulus generator of claim 13, further comprising means to maintain the obtained stimulation rate within selected maximum and minimum rate limits.

24. The stimulus generator of claim 23, further comprising means to reduce the obtained stimulation rate from said maximum rate limit after cessation of exercise by the patient.

25. A pulse generator controller for variably controlling the pacing rate of a cardiac pacer, comprising:
  means for detecting the central venous blood temperature of the pacer patient:
  means for calculating components of the desired pacing rate related to the detected blood temperature, a moving dynamic reference temperature having a changing value dependent on rate of variation of the detected blood temperature relative to a preselected rate of variation, and a static reference temperature, said components consisting of (i) a predetermined reference rate related to a baseline value of the blood temperature, (ii) a natural rate response related to variations of the blood temperature with the patient's circadian rhythm and other non-exercise phenomena relative to the static reference temperature, (iii) a dynamic rate response related to variations of the blood temperature with patient exercise relative to the moving dynamic reference temperature, and (iv) a step rate response related to variations of the blood temperature with onset of patient exercise; and
  means for combining the calculated components to establish a physiologically appropriate pacing rate, with the contributions of components (ii), (iii) and (iv) being based on the recited variations of the blood temperature.

26. In a stimulus generator for varying the pacing rate of a cardiac pacer according to the physiological state of the patient, wherein said pacer is of the type responsive to variations in the detected blood temperature with respect to a reference temperature, the improvement comprising means for periodically recalculating said reference temperature as a long term weighted average over a selectable interval.

27. A method for variably controlling the pacing rate of a cardiac pacer comprising the steps of:
  detecting the patient's central venous blood temperature;
  determining a moving dynamic reference temperature that establishes a moving temperature reference value from which to measure that current change in blood temperature indicative of the metabolic need and means to adequately adjust the pacing rate accordingly;
  calculating a dynamic heart rate response related to variations in said detected blood temperature relative to said dynamic reference temperature, attributable to patient exercise; and
  combining said dynamic rate response with a predetermined base rate to obtain a desired pacing rate.

28. The method defined in claim 27, further including the steps of
  establishing a relatively static reference temperature;
  calculating a natural heart rate response related to non-exercise related variations in said detected blood temperature relative to said static reference temperature; and
  combining said natural rate response with said dynamic rate response and said base rate to obtain said desired pacing rate.

29. The method defined in claim 28, further including the step of periodically recalculating said static reference temperature as a long-term weighted average temperature over a selectable interval.

30. The method defined in claim 27, further including the steps of:
  calculating a step rate response;
  determining whether preselected criteria indicative of the onset of patient exercise are satisfied; and
  if said criteria are satisfied, combining said step rate response with said dynamic rate response and said base rate to obtain said desired pacing rate.

31. The method defined in claim 30 wherein said preselected criteria include criteria related to the magnitude and slope of a detected drop in said blood temperature.

32. The method defined in claim 30 wherein said preselected criteria include criteria related to the present pacing rate, and to the relative difference between said blood temperature and said dynamic reference temperature during a predetermined interval preceding the calculation of said step rate response.

33. The method defined in claim 27, further including the step of limiting the rate of change of the pacing rate obtained from said combining step.

34. The method defined in claim 27, further including the step of maintaining the pacing rate obtained from the combining step within selected maximum and minimum rate limits.

35. The method defined in claim 34, further including the step of the obtained pacing rate from said maximum rate limit after cessation of exercise by the patient.

36. A stimulus generator for a rate adaptive cardiac pacemaker, comprising
    means for detecting a physiological parameter of a pacemaker patient uniquely indicative of either patient exercise or non-exercise,
    means responsive to said parameter for processing thereof according to a first algorithm in which heart rate is a function of said parameter under conditions of exercise by a healthy person with a normally functioning heart,
    means responsive to said parameter for processing thereof according to a second algorithm in which heart rate is a function of said parameter under conditions of non-exercise by a healthy person with a normally functioning heart,
    means for generating electrical stimuli at a controllably variable rate, and
    means responsive to said detected parameter for selectively combining said first and second algorithms to control the rate at which stimuli are generated by said generating means, said combining means including means for selectively determining the contribution of each of said first and second algorithms to control the stimulation rate.

37. The stimulus generator of claim 36, further comprising
    means responsive to said detected parameter for determining the onset of patient exercise, and means responsive to that determination for stepping up the rate at which stimuli are generated by said generating means.

38. The stimulus generator of claim 36, wherein said parameter is blood temperature variation relative to a reference temperature.

39. The stimulus generator of claim 38, wherein the processing means for the first algorithm includes means for developing a variable reference temperature having an instantaneous value dependent on detected blood temperature and the variation thereof relative to a predetermined rate of variation.

40. The stimulus generator of claim 39, wherein said contribution determining means utilizes the instantaneous value of said variable reference temperature relative to the detected blood temperature to selectively determine the contribution of the first and second algorithms to the rate control.

41. The stimulus generator of claim 39 wherein said combining means further includes means for rapidly adjusting the variable reference temperature to track detected blood temperature to lower value, and for gradually adjusting the variable reference temperature toward detected blood temperature of higher value when the detected blood temperature variation is below said predetermined rate of variation.

42. The stimulus generator of claim 38 wherein the processing means for the second algorithm includes means for establishing a relatively static reference temperature against which variations of the detected blood temperature are to be measured.

43. The stimulus generator of claim 42 wherein said establishing means periodically recalculates said static reference temperature as a long-term weighted average over a programmable interval.

44. The stimulus generator of claim 36 wherein said contribution determining means designates a contribution of said first algorithm to the rate control only if the detected parameter is indicative of patient exercise.

45. An exercise responsive cardiac pacemaker, comprising
    means for detecting the commencement and continuation of patient exercise by monitoring the timely course o a physiological parameter,
    means for generating electrical stimuli at a controllable rate,
    means responsive to said detection for controlling the rate at which stimuli are generated by said generating means according to a physiological function representing a combination of an initial temporary increase in heart rate from a non-exercise related heart rate at the moment of detection of commencement of exercise, with selectively variable contributions to rate control attributable to exercise related and non-exercise related components in which heart rate is a function of said physiological parameter in the manner experienced by a healthy person with a normal functioning heart, throughout the detected exercises, and
    means for selectively varying the contributions of said exercise related and non-exercise related heart rate components to the rate control.

* * * * *